US009296995B2

(12) United States Patent
Geurtsen et al.

(10) Patent No.: US 9,296,995 B2
(45) Date of Patent: Mar. 29, 2016

(54) **VACCINES AGAINST *BORDETELLA PERTUSSIS* BASED ON LPS GLYCOSYLTRANSFERASE MUTANTS**

(75) Inventors: Jeroen Johannes Gerardus Geurtsen, Vleuten (NL); Johannes Petrus Maria Tommassen, Utrecht (NL); Peter André Van Der Ley, Utrecht (NL)

(73) Assignee: DE STAAT DER NEDERLANDEN, VERT. DOOR DE MINISTER VAN VWS, The Hague (NL)

( * ) Notice: Subject to any disclaimer, the term of this patent is extended or adjusted under 35 U.S.C. 154(b) by 774 days.

(21) Appl. No.: 12/593,346

(22) PCT Filed: Mar. 25, 2008

(86) PCT No.: PCT/NL2008/050169
§ 371 (c)(1),
(2), (4) Date: Feb. 1, 2010

(87) PCT Pub. No.: WO2008/118015
PCT Pub. Date: Oct. 2, 2008

(65) Prior Publication Data

US 2010/0291153 A1 Nov. 18, 2010

(30) Foreign Application Priority Data

Mar. 26, 2007 (EP) .................................... 07104885

(51) Int. Cl.
*C12N 9/10* (2006.01)
*A61K 39/02* (2006.01)
*A61K 39/10* (2006.01)
*A61K 39/00* (2006.01)

(52) U.S. Cl.
CPC ............... *C12N 9/1048* (2013.01); *A61K 39/00* (2013.01); *A61K 39/099* (2013.01)

(58) Field of Classification Search
CPC .............................. A61K 39/00; C12N 9/1048
USPC .................. 424/254.1, 93.2, 94.5; 435/320.1, 435/252.1, 193
See application file for complete search history.

(56) References Cited

U.S. PATENT DOCUMENTS

2004/0029129 A1* 2/2004 Wang et al. ....................... 435/6
2008/0274145 A1 11/2008 Tommassen et al.

FOREIGN PATENT DOCUMENTS

WO 2006065139 A 6/2006

OTHER PUBLICATIONS

Stibitz et al. Methods Enzymol. 235: 458-465, 1994.*
Reckseidler et al. Infect. Immun. 69: 134-144, 2001.*
Seffernick et al. J. Bacteriol. 183: 2405-2410, Apr. 2001.*
Skolnick et al. Trends in Biotechnology 18: 34-39, 2000.*
Parkhill et al.,"Comparative analysis of the genome sequences of Bordetella pertussis, Bordetella parapertussis and Bordetella bronchiseptica," Nature Genetics, 2003, 35: 32-40.
Q7VWC9 (Sequence Database) "Putative transferase," 2003, retrieved from EBI accession No. UNIPROT: Q7VWC9.
Sebaihia et al."Comparison of the genome sequence of the poultry pathogen *Bordetella avium* with those of *B. bronchiseptica*, *B. pertussis*, and *B. parapertussis* reveals extensive diversity in surface structures associated with host interaction," Journal of Bacteriology, 2006, 188:6002-6005.
Q2KYR3 (Sequence Database) , "Lipopolysaccharide core biosynthesis glycosyl transferase," 2006, retrieved from EBI accession No. UNIPROT:Q2KYR3.
Preston et al.,"The molecular genetics and role in infection of lipopolysaccharide biosynthesis in the Bordetellae," Journal of Endotoxin Research, 2001, 7:251-261.
A. Preston & D. Maskell, "The Molecular Genetics and Role in Infection of Lipopolysaccharide Biosynthesis in the Bordetellae", J. Endotoxin Research 7:251-261(2001).

* cited by examiner

*Primary Examiner* — S. Devi
(74) *Attorney, Agent, or Firm* — Browdy and Neimark, PLLC

(57) ABSTRACT

The invention relates to an improved vaccine against *pertussis* wherein mutants of *Bordetella pertussis* having a modified LPS molecule or the obtainable LPS molecules are used. These mutants or the obtainable LPS molecules may further be used as an adjuvant.

18 Claims, 8 Drawing Sheets

A

B

B

A

B

SEQUENCE LISTING

```
<160> NUMBER OF SEQ ID NOS: 14

<210> SEQ ID NO 1
<211> LENGTH: 283
<212> TYPE: PRT
<213> ORGANISM: Bordetella pertussis
```

<400> SEQUENCE: 1

```
Met Arg Asn Ala Pro Asn Val Pro Val Leu Met Tyr His His Val Thr
1               5                   10                  15

Pro Ala Gly Gly Met Ile Ala Ala Thr Pro Glu Val Phe Glu Arg Gln
            20                  25                  30

Ile Ala Ala Leu Ala Arg Ala Gly Tyr Arg Ser Leu Gly Thr Ala Glu
        35                  40                  45

Phe Ala Ala Tyr Leu Asp Gly Ala Pro Val Pro Glu Lys Ser Val Leu
    50                  55                  60

Ile Thr Phe Asp Asp Gly Tyr Leu Asn Asn Trp Val Tyr Ala His Pro
65                  70                  75                  80

Ile Leu Gln Arg His Gly Met Lys Ala Val Leu Phe Leu Ile Thr Gly
                85                  90                  95

Leu Leu Gly Asp Gly Pro Ala Arg Pro Cys Ala Gly Gln Asp Gly Pro
            100                 105                 110

Leu Pro Pro Ala Pro Asp His Asp Glu Ser Lys Arg Leu Ile Ala Ala
        115                 120                 125

Gly Arg Ala Asp Glu Val Met Leu Arg Trp Ser Glu Val Gln Ala Met
    130                 135                 140

Leu Ala Ala Gly Thr Phe Glu Val His Ser His Thr His Thr His Thr
145                 150                 155                 160

Arg Trp Asp Lys Gln Cys Gly Pro Asp Val Ala Ala Lys Arg Ala His
                165                 170                 175

Ile Val Gln Glu Leu Ala Asp Ser Arg Arg Ala Leu Gln Ala Arg Leu
            180                 185                 190

Gly Glu Val Ser Asp His Leu Cys Trp Pro Gln Gly Tyr Phe Asp Ala
        195                 200                 205

Asp Tyr Val Gln Ala Ala Arg Asp Ala Gly Phe Arg His Leu Tyr Thr
    210                 215                 220

Thr Asp Ala Leu Gly Gln Asn Val Pro Gly Gly Asp Pro Ala His Ile
225                 230                 235                 240

Tyr Arg Phe Ala Val Arg Asn Arg Ala Gly Gly Trp Leu Asn Arg Arg
                245                 250                 255

Ile Trp Leu Ala Arg His Pro Trp Ile Gly Pro Arg Tyr His Ala Trp
            260                 265                 270

Lys Ala Trp Lys Lys Lys Leu Arg Arg Arg Ala
        275                 280
```

<210> SEQ ID NO 2
<211> LENGTH: 367
<212> TYPE: PRT
<213> ORGANISM: Bordetella pertussis

<400> SEQUENCE: 2

```
Met Arg Pro Leu Arg Ile Val His Ser Glu Ala Ala Thr Ser Phe Gly
1               5                   10                  15

Gly Gln Glu Gly Arg Ile Phe Lys Glu Met Thr Ala Met Arg Glu Arg
            20                  25                  30

Gly His His Met Glu Ala Ile Cys Gln Pro Gln Ala Gln Leu Ala Arg
        35                  40                  45

Arg Leu Ala Glu Ala Ser Phe Thr Val His Thr Leu Glu Met Asp Gly
    50                  55                  60

Pro Arg Asn Tyr Leu Arg Gly Val Leu Ser Leu Arg Arg Leu Leu Arg
65                  70                  75                  80
```

-continued

```
Gln Gly Arg Tyr Asp Val Leu Asn Thr His Ser Arg Arg Asp Thr Val
                85                  90                  95

Ile Ala Ala Ala Ala Gly Arg Leu Ala Gly Thr Pro Leu Ile Val Arg
            100                 105                 110

Thr Arg His Leu Ser Asn Arg Val Gly Ser Leu Trp Ser Tyr Thr Gly
        115                 120                 125

Leu Pro His Arg Val Thr Thr Val Ser Asp His Val Arg Gln His Leu
    130                 135                 140

Ile Glu Arg Gly Val Pro Ala Gly His Ile Ala Thr Val Tyr Ser Pro
145                 150                 155                 160

Ile Val Leu Pro Pro Pro Ile Glu His Ser Thr Leu Arg Gly Glu Leu
                165                 170                 175

Gly Leu Ala Ala Asp Asp Ile Val Val Gly Cys Val Ala Val Met Arg
            180                 185                 190

Ala Thr Lys Gly His Arg Glu Leu Ile Asp Ala Met Arg Pro Leu Met
        195                 200                 205

Ala Glu Arg Ala Asn Leu His Leu Val Phe Val Gly Gly Gly Ser Pro
    210                 215                 220

Met Phe Glu Gln Thr Gln Ala Tyr Val Ala Glu Leu Gly Leu Gln Ala
225                 230                 235                 240

Arg Ile His Leu Met Gly Thr Arg Asn Asp Val Pro Asn Leu Leu Ala
                245                 250                 255

Gly Phe Asp Leu Phe Ala Leu Ala Thr Arg Gln Glu Ala Ser Gly Thr
            260                 265                 270

Val Tyr Val Glu Ala Glu Ala Cys Gly Leu Pro Val Val Gly Thr Asp
        275                 280                 285

Val Gly Gly Val Ser Glu Met Met Arg Asp Gly Glu Thr Gly Ile Leu
    290                 295                 300

Val Pro Val Asp Asp Pro Ala Ala Leu Gly Ala Ala Leu Arg Arg Leu
305                 310                 315                 320

Ile Asp Asp Arg Ala Leu Arg Arg Arg Met Gly Glu Ala Gly Arg Arg
                325                 330                 335

Met Val Arg Asp Glu Lys Val Phe Ala Pro Glu Arg Leu Ala Glu Arg
            340                 345                 350

Thr Glu Ala Ile Tyr Arg Gln Trp Leu Ala Glu Arg Gly His Ala
        355                 360                 365
```

<210> SEQ ID NO 3
<211> LENGTH: 852
<212> TYPE: DNA
<213> ORGANISM: Bordetella pertussis

<400> SEQUENCE: 3

```
atgcgtaacg cgcccaatgt cccggtgctg atgtaccacc acgtcacccc ggccggcggc      60

atgatcgccg ccacgcccga ggtgttcgaa cggcagatcg ccgcgctggc gcgggccggc     120

taccgctcgc tgggcacggc cgagttcgcc gcctacctgg acggcgcccc ggtgcccgag     180

aaatcggtgc tgatcacctt cgacgacgga tacctgaaca actgggtgta tgcccacccg     240

atcctgcagc gccacggcat gaaggccgtg ctgttcctga tcaccggcct gctgggcgat     300

ggtccggcgc ggccctgcgc cgggcaggac gggccgctgc cgcccgcgcc cgaccacgac     360

gaaagcaagc gcctgatcgc cgccggacgc gccgacgagg tcatgctgcg ctggagcgaa     420

gtgcaggcca tgctggcggc gggcaccttc gaggtgcatt cgcacaccca tacccatacg     480

cgctgggaca agcagtgcgg ccccgacgtc gccgccaagc gcgcccatat cgtccaggag     540
```

ctggccgatt cgcgccgggc gctgcaggcc cggctgggcg aggtcagcga ccacctgtgc 600
tggccccagg gctatttcga cgccgactat gtgcaggcgg cgcgcgacgc cggctttcgc 660
catctctaca ccaccgacgc cctgggccag aacgtcccgg gcggcgatcc cgcacacata 720
taccgcttcg cggtgcgcaa ccgcgccggc ggctggctca accgccgcat ctggctggcg 780
cgccatccct ggatcggccc gcgctatcac gcctggaagg cctggaagaa aaagctgagg 840
aggcgcgcat ga 852

<210> SEQ ID NO 4
<211> LENGTH: 1104
<212> TYPE: DNA
<213> ORGANISM: Bordetella pertussis

<400> SEQUENCE: 4
atgcggccat tgcgtatcgt gcattccgaa gccgccacca gtttcggcgg ccaggaaggg 60
cgcatcttca aggaaatgac ggccatgcgc gagcgcggcc atcacatgga ggcgatctgc 120
cagccgcagg cccagctggc gcgccgcctg gccgaggcca gcttcaccgt gcacacgctg 180
gaaatggacg ggccgcgcaa ttacctgcgc ggcgtgctga gcctgcgccg cctgctgcgc 240
cagggccgct acgacgtgct gaacacgcac agcccggcgcg ataccgtgat cgccgcggcc 300
gccggccggc tggcgggcac gccgctgatc gtgcgtaccc gccacctgtc caacagggtc 360
ggctcgctct ggtcctatac cgggctgccg caccgcgtca ccacggtcag cgaccacgtg 420
cgccagcacc tcatcgaacg cggcgtaccc gccggccata tcgccacggt gtattcgccc 480
atcgtgctgc cgcctcccat cgaacactcg accctgcgcg gcgagctggg cctggcggcc 540
gacgatatcg tggtcggctg cgtggcggtg atgcgcgcca ccaaggggca ccgcgaactc 600
atcgacgcca tgcggccgct gatggccgag cgtgccaacc tgcacctggt gttcgtcggc 660
ggcggctcgc cgatgttcga gcagacccag gcctacgtgg ccgaactggg cctgcaggcg 720
cgcatccacc tgatgggcac gcgcaacgac gtccccaacc tgctggccgg tttcgacctg 780
ttcgccctgg ccacccgcca ggaggcttcg ggcaccgtct atgtcgaggc cgaagcctgt 840
ggcctgccgg tcgtcggcac cgacgtgggc ggcgtgtccg agatgatgcg cgatggcgag 900
accggcatcc tggtgccggt ggacgacccg gcggcgctgg gcgccgcgct gcgccgcctg 960
atcgacgacc gcgcgttgcg gcgccgcatg ggcgaggccg gccggcgcat ggtgcgcgac 1020
gaaaaggtct tcgcgcccga acggctggcc gagcgcaccg aggccatcta ccggcagtgg 1080
ctggcggagc gcggccatgc gtaa 1104

<210> SEQ ID NO 5
<211> LENGTH: 20
<212> TYPE: DNA
<213> ORGANISM: artificial
<220> FEATURE:
<223> OTHER INFORMATION: primer

<400> SEQUENCE: 5
ttccgcactt actggctgag 20

<210> SEQ ID NO 6
<211> LENGTH: 25
<212> TYPE: DNA
<213> ORGANISM: artificial
<220> FEATURE:
<223> OTHER INFORMATION: primer

<400> SEQUENCE: 6
ggatcctcgc ggtacgacag cacat 25

<210> SEQ ID NO 7
<211> LENGTH: 26
<212> TYPE: DNA
<213> ORGANISM: artificial
<220> FEATURE:
<223> OTHER INFORMATION: primer

<400> SEQUENCE: 7
ggatcctgtt gcgcgagatg ctggag 26

<210> SEQ ID NO 8
<211> LENGTH: 20
<212> TYPE: DNA
<213> ORGANISM: artificial
<220> FEATURE:
<223> OTHER INFORMATION: primer

<400> SEQUENCE: 8
cctcatcgcc aaggtcaatc 20

<210> SEQ ID NO 9
<211> LENGTH: 20
<212> TYPE: DNA
<213> ORGANISM: artificial
<220> FEATURE:
<223> OTHER INFORMATION: primer

<400> SEQUENCE: 9
tcaccttcga cgacggatac 20

<210> SEQ ID NO 10
<211> LENGTH: 25
<212> TYPE: DNA
<213> ORGANISM: artificial
<220> FEATURE:
<223> OTHER INFORMATION: primer

<400> SEQUENCE: 10
ggatccgtgc gcatctacct gatcc 25

<210> SEQ ID NO 11
<211> LENGTH: 24
<212> TYPE: DNA
<213> ORGANISM: artificial
<220> FEATURE:
<223> OTHER INFORMATION: primer

<400> SEQUENCE: 11
ggatccgaat cgaccacgat gaac 24

<210> SEQ ID NO 12
<211> LENGTH: 20
<212> TYPE: DNA
<213> ORGANISM: artificial
<220> FEATURE:
<223> OTHER INFORMATION: primer

<400> SEQUENCE: 12
gatccagctt ggcctggttg 20

-continued

```
<210> SEQ ID NO 13
<211> LENGTH: 20
<212> TYPE: DNA
<213> ORGANISM: artificial
<220> FEATURE:
<223> OTHER INFORMATION: primer

<400> SEQUENCE: 13

gtgacgtggt ggtacatcag                                              20


<210> SEQ ID NO 14
<211> LENGTH: 20
<212> TYPE: DNA
<213> ORGANISM: artificial
<220> FEATURE:
<223> OTHER INFORMATION: primer

<400> SEQUENCE: 14

tggtctaccg caggaacaat                                              20
```

VACCINES AGAINST *BORDETELLA PERTUSSIS* BASED ON LPS GLYCOSYLTRANSFERASE MUTANTS

FIELD OF THE INVENTION

The invention relates to an improved vaccine against *pertussis* comprising mutants of *Bordetella pertussis* having a modified LPS molecule and/or the LPS molecules obtainable from these mutants. These mutants and/or the obtainable LPS molecules may further be used as an adjuvant.

BACKGROUND OF THE INVENTION

LPS is an amphiphilic molecule located in the outer leaflet of the outer membrane of Gram-negative bacteria. LPS possesses both endotoxic activity and adjuvant activity. Both properties are based upon its recognition by the host TLR4/MD-2 receptor complex (reviewed in Pålsson-McDermott and O'Neill, 2004; O'Neill, 2006). LPS consists of three distinct structural domains: lipid A, the core, and the O-antigen. Lipid A functions as a hydrophobic membrane anchor and forms the bioactive component of the molecule (Takada and Kotani, 1989). The core region consists of a complex oligosaccharide, which, as compared to the O-antigen, shows only limited structural variability. In some bacteria, e.g., Enterobacteriaceae, the core oligosaccharide (core OS) can be divided into an inner core and an outer core. The outer core primarily consists of pyranosidic hexoses, e.g., D-glucose, D-galactose, and D-glucosamine, whereas the inner core primarily consists of octulosonic acids and heptopyranoses. In the vast majority of Gram-negative bacteria, the core domain is connected to the lipid A domain by a specific carbohydrate, 2-keto-3-deoxyoctulosonic acid (Kdo) (Raetz and Whitfield, 2002). The O-antigen comprises the most variable part of the LPS and confers bacteria serotype specificity. It is composed of repeating sugar subunits of one to eight sugars. Each O-chain can contain up to 50 of these subunits. The O-antigen has been implicated in bacterial immune escape, especially the escape from serum complement-mediated lysis (Raetz and Whitfield, 2002).

In contrast to the LPS of *Bordetella bronchiseptica* and *Bordetella parapertussis*, the LPS of *Bordetella pertussis* never contains an O-antigen domain (Peppler, 1984; Di Fabio et al., 1992). Therefore, *B. pertussis* LPS is often referred to as lipooligosaccharide. *B. pertussis* produces two dominant LPS forms, band A and band B LPS (Peppler, 1984). Band B LPS is composed of lipid A and a core oligosaccharide consisting of 9 carbohydrates (Caroff et al., 2000). Addition of a terminal trisaccharide, consisting of N-acetyl glucosamine, 2,3-diacetamido-2,3-dideoxy-mannuronic acid, and 2-acetamido-4-N-methyl-2,4-dideoxy-fucose, to band B LPS forms the LPS referred to as band A.

In *Escherichia coli* and *Salmonella enterica* serovar Typhimurium, the core OS biosynthesis gene cluster consists of three operons, designated the gmhD, waaQ, and WaaA operons. The gmhD operon consists of four genes, gmhD and waaFCL, which are involved in the synthesis of the inner core (Schnaitman and Klena, 1993). The gmhD, waaF, and waaC genes encode proteins involved in the biosynthesis and transfer of Heptoses I and II to $Kdo_2$-lipid A (Schnaitman and Klena, 1993), whereas the waaL gene product is a ligase that is involved in the attachment of the O-antigen (MacLachlan et al., 1991). The waaQ operon is the largest of the three operons and encodes proteins that are involved in the biosynthesis of the outer core and in modification/decoration of the core OS. The number and types of genes present within in the waaQ operon differs per strain, which explains the strain-specific differences in core composition (Heinrichs et al., 1998). The waaA operon often encodes only one protein, KdtA. Only in *E. coli* K-12, an additional non LPS-related open reading frame (ORF) is present (Raetz and Whitfield, 2002). The kdtA gene of Enterobacteriaceae encodes the bifunctional Kdo transferase that adds the two Kdo residues in the $Kdo_2$-lipid A biosynthesis (Clementz and Raetz, 1991).

Although the *Bordetella* and *E. coli* core OS show some resemblance, the exact composition and configuration of residues display marked differences. For example, the *Bordetella* core OS contains only one Kdo residue, instead of the two or three residues that are found in most other Gram-negative bacteria, including *E. coli*. Recently, this was shown to be due to the functioning of *Bordetella* KdtA as a monofunctional, rather than as a bifunctional Kdo transferase (Isobe et al., 1999). The enzymes responsible for the synthesis of the remaining portion of the *Bordetella* core OS are currently unknown and await further identification.

Although its lipid A part is generally seen as the main determinant for the biological activity of LPS through the activation of the TLR4/MD-2 receptor complex, the oligosaccharide region can also play an important role in its interaction with antigen-presenting cells (APCs). Receptors implicated in this type of LPS recognition include the complement receptor CR3 and the scavenger receptor SR-A (van Amersfoort et al., 2003; Plüddemann et al., 2006).

Several *Bordetella pertussis* vaccines were already used. Introduction of whole-cell *pertussis* (wP) vaccines in the 1940s and 1950s, and later of acellular *pertussis* (aP) vaccines in the 1980s and 1990s, led to a gradual decline in *pertussis* incidence and reduced morbidity and mortality of the disease to low levels. Despite high vaccination coverage, *pertussis* disease has remained endemic and kept showing a cyclic pattern with peaks in incidence every 2 to 5 years. During the last two decades, several countries, including the Netherlands, have experienced increases in numbers of reported *pertussis* cases. Interestingly, in some areas, a shift in age distribution has also been observed. Whereas in the pre-vaccination and early vaccine era *pertussis* cases were predominantly reported in young children, adults and adolescents have accounted for an increasing proportion of the cases in recent years. Several reasons for the re-emergence of reported *pertussis* have been proposed, including: (1) genetic changes in circulating *B. pertussis* strains that decrease vaccine efficacy, (2) reduced potency of *pertussis* vaccines, (3) waning immunity, (4) increased reporting of *pertussis* cases, and (5) the improved diagnosis of *pertussis* disease.

Therefore, there is still a need for new vaccines against *Bordetella pertussis* which does not exhibit all the drawbacks of the existing vaccines.

DESCRIPTION OF THE INVENTION

The present invention is based on the hypothesis that *B. pertussis* mutants with an altered oligosaccharide chain might be affected in their interaction with dendritic cells (DC)s. Specific targeting to antigen presenting cells (APC)s, such as DCs, could conceivably affect the outcome of the immune response against a whole-cell *pertussis* vaccine. As a first step towards improvement of whole-cell vaccines by this route, we have now identified a gene cluster involved in LPS oligosaccharide biosynthesis in *B. pertussis*. Especially two genes within this cluster when inactivated or overexpressed give mutants having an improved potentiality to interact with and activate DC.

Polypeptides

In a first aspect, the invention provides two polypeptides.

The first polypeptide is a polysaccharide deacetylase and has an amino acid sequence with at least 50% identity with the amino acid sequence of SEQ ID NO:1.

The second polypeptide is a glycosyltransferase and has an amino acid sequence with at least 50% identity with the amino acid sequence of SEQ ID NO:2.

The activity of the polysaccharide deacetylase respectively of the glycosyltransferase polypeptide is preferably assessed by overexpressing respectively inactivating the respective encoded gene in a *Bordetella pertussis* strain as later defined herein and analyzing the obtainable LPS. When the LPS produced by the transformed *Bordetella pertussis* strain comprises at least detectable amounts of the LPS of the invention as later defined herein, the polysaccharide deacetylase, respectively the glycosyltransferase polypeptides would be said to be active and functional. Detectable amounts of LPS are preferably detectable as described in the examples: after isolation with hot phenol/water extraction (Westphal and Jann, 1965), O-deacylation by mild hydrolysis (Holst 2000) and analysis by ESI-MS (Electrospray-ionization Mass spectrometry) in the negative ion-mode.

According to an even more preferred embodiment, the polypeptide has at least 50%, 55%, 60%, 65%, 70%, 75%, 80% or 85%, even more preferably at least 90%, 92%, 95%, 97%, 98% or 99% identity with the amino acid sequence of SEQ ID NO:1. In a most preferred embodiment, the polysaccharide deacetylase has the SEQ ID NO:1. This polysaccharide deacetylase originates from *Bordetella pertussis*. The nucleic acid sequence coding for the amino acid sequence of SEQ ID NO:1 is given in SEQ ID NO:3.

According to another even more preferred embodiment, the polypeptide has at least 50%, 55%, 60%, 65%, 70%, 75%, 80% or 85%, even more preferably at least 90%, 92%, 95%, 97%, 98% or 99% identity with the amino acid sequence of SEQ ID NO:2. In a preferred embodiment, the glycosyltransferase has the SEQ ID NO:2. This glycosyltransferase originates from *Bordetella pertussis*. The nucleic acid sequence coding for the amino acid sequence of SEQ ID NO:2 is given in SEQ ID NO:4. Percentage of identity is calculated as the number of identical amino acid residues between aligned sequences divided by the length of the aligned sequences minus the length of all the gaps. Multiple sequence alignment was performed using DNAman 4.0 optimal alignment program using default settings. The alignment is usually performed between sequences identified by their SEQ ID NO or parts thereof. Preferably, the alignment is carried out using sequences identified by their SEQ ID NO.

The skilled person will understand that the polypeptides of the present invention could be obtained from other organisms than *Bordetella pertussis* as long as they have the required activity and identity. In a preferred embodiment, each polypeptide as identified above is obtained from a *Bordetella* species such as *pertussis, bronchiseptica, parapertussis*. Most preferably, each polypeptide as identified above is obtained from *Bordetella pertussis*. One single *Bordetella pertussis* strain or several distinct *Bordetella pertussis* strains may have several homologues polypeptides according to the present invention.

According to another preferred embodiment, the polypeptide of the invention, is a variant of any one of the polypeptide sequences as defined before. A variant polypeptide may be a non-naturally occurring form of the polypeptide. A polypeptide variant may differ in some engineered way from the polypeptide isolated from its native source. A variant may be made by site-directed mutagenesis starting from the amino acid sequence of SEQ ID NO:1 or from SEQ ID NO:2 or from the nucleic acid sequence encoding the amino acid sequence of SEQ ID NO:1, which is SEQ ID NO:3, or from the nucleic acid sequence encoding the amino acid sequence of SEQ ID NO:2, which is SEQ ID NO:4. Preferably, the polypeptide variant contains mutations that do not alter the biological function of the encoded polypeptide. Biological function or activity of either the polysaccharide deacetylase or the glycosyltransferase has already been defined herein.

In another aspect of the invention, there is provided a polysaccharide deacetylase, respectively a glycosyltransferase as earlier defined both being for use for preparing a medicament. Preferably said medicament is a vaccine or an adjuvant as later defined herein.

Nucleic Acid Sequences

In a second aspect of the invention, there are provided two nucleic acid sequences. The first one codes for a polysaccharide deacetylase having an amino acid sequence with at least 50% identity with the amino acid sequence of SEQ ID NO:1, preferably having the amino acid sequence SEQ ID NO:1, and/or originating from a *Bordetella* species, preferably *Bordetella pertussis.*

The first nucleic acid sequence is preferably a nucleic acid sequence having at least 50% identity with the nucleic acid sequence of SEQ ID NO:3. Preferably, the identity is of at least 55%, more preferably at least 60%, more preferably at least 65%, more preferably at least 70%, more preferably at least 75%, more preferably at least 80%, more preferably at least 85%, more preferably at least 90%, even more preferably at least 95%, even more preferably at least 98% and even more preferably at least 99%. Most preferably, the nucleic acid sequence has the nucleic acid sequence of SEQ ID NO:3. SEQ ID NO:3 corresponds to NP_8809668.

The second nucleic acid sequence codes for a glycosyltransferase having an amino acid sequence with at least 50% identity with the amino acid sequence of SEQ ID NO:2, preferably having the amino acid sequence SEQ ID NO:2, and/or originating from a *Bordetella* species, preferably *Bordetella pertussis.*

The second nucleic acid sequence is preferably a nucleic acid sequence having at least 50% identity with the nucleic acid sequence of SEQ ID NO:4. Preferably, the identity is of at least 55%, more preferably at least 60%, more preferably at least 65%, more preferably at least 70%, more preferably at least 75%, more preferably at least 80%, more preferably at least 85%, more preferably at least 90%, even more preferably at least 95%, even more preferably at least 98% and even more preferably at least 99%. Most preferably, the nucleic acid sequence has the nucleic acid sequence of SEQ ID NO:4. SEQ ID NO:4 corresponds to NP_8809669.

Percentage of identity was determined by calculating the ratio of the number of identical nucleotides in the sequence divided by the length of the total nucleotides minus the lengths of any gaps. DNA multiple sequence alignment was performed using DNAman version 4.0 using the Optimal Alignment (Full Alignment) program. The minimal length of a relevant DNA sequence showing 50% or higher identity level should be 40 nucleotides or longer. The alignment is usually performed between sequences identified by their SEQ ID NO or parts thereof. Preferably, the alignment is carried out using sequences identified by their SEQ ID NO.

According to another preferred embodiment, the nucleic acid sequence of the invention is a variant of any of the nucleic acid sequences as defined above. Nucleic acid sequence variants may be used for preparing polypeptide variants as defined earlier. A nucleic acid variant may be a fragment of any of the nucleic acid sequences as defined above. A nucleic acid variant may also be a nucleic acid sequence that differs from SEQ ID NO:3 or SEQ ID NO:4 by virtue of the degeneracy of the genetic code. A nucleic acid variant may also be an allelic variant of SEQ ID NO:3 or SEQ ID NO:4. An allelic variant denotes any of two or more alternative forms of a gene occupying the same chromosome locus. A preferred nucleic acid variant is a nucleic acid sequence, which contains silent mutation(s). Alternatively or in combination, a nucleic acid variant may also be obtained by introduction of nucleotide substitutions, which do not give rise to another amino acid sequence of the polypeptide encoded by the nucleic acid sequence, but which corresponds to the codon usage of the host organism intended for production of the polypeptide of the invention. According to a preferred embodiment, the nucleic acid variant encodes a polypeptide still exhibiting its biological function as earlier defined herein. More preferably, the nucleic acid sequence variant encodes a polypeptide exhibiting polysaccharide deacetylase or glycosyltransferase activity respectively. Nucleic acid sequences encoding such a polypeptide may be isolated from any microorganism.

All these variants can be obtained using techniques known to the skilled person, such as screening of library by hybridisation (southern blotting procedures) under low to medium to high hybridisation conditions with for the nucleic acid sequence SEQ ID NO:3 or SEQ ID NO:4 or a variant thereof which can be used to design a probe. Low to medium to high stringency conditions means prehybridization and hybridization at 42° C. in 5×SSPE, 0.3% SDS, 200 μg/ml sheared and denatured salmon sperm DNA, and either 25% 35% or 50% formamide for low to medium to high stringencies respectively. Subsequently, the hybridization reaction is washed three times for 30 minutes each using 2×SSC, 0.2% SDS and either 55° C., 65° C., or 75° C. for low to medium to high stringencies.

The sequence information as provided herein should not be so narrowly construed as to require inclusion of erroneously identified bases. The skilled person is capable of identifying such erroneously identified bases and knows how to correct for such errors.

In another aspect of the invention, there is provided a nucleic acid coding for a polysaccharide deacetylase, respectively a glycosyltransferase as earlier defined both nucleic acids being for use for preparing a medicament. Preferably said medicament is a vaccine or an adjuvant as later defined herein.

Nucleic Acid Construct

In a further aspect, the invention relates to a nucleic acid construct comprising any of the nucleic acid sequences defined in the former section, said nucleic acid sequence encoding a polypeptide exhibiting:

- polysaccharide activity and having an amino acid sequence which has at least 50% identity with the amino acid sequence of SEQ ID NO:1 or
- glycosyltransferase activity and having an amino acid sequence which has at least 50% identity with the amino acid sequence of SEQ ID NO:2.

Optionally, the nucleic acid sequence present in the nucleic acid construct is operably linked to one or more control sequences, which direct the production of the polypeptide in a suitable expression host.

Operably linked is defined herein as a configuration in which a control sequence is appropriately placed at a position relative to the nucleic acid sequence coding for the polypeptide of the invention such that the control sequence directs the production of the polypeptide of the invention.

Expression will be understood to include any step involved in the production of the polypeptide including, but not limited to transcription, post-transcriptional modification, translation, post-translational modification and secretion.

Nucleic acid construct is defined as a nucleid acid molecule, which is isolated from a naturally occurring gene or which has been modified to contain segments of nucleic acid which are combined or juxtaposed in a manner which would not otherwise exist in nature.

Control sequence is defined herein to include all components, which are necessary or advantageous for the expression of a polypeptide. At a minimum, the control sequences include a promoter and trancriptional and translational stop signals.

Expression Vector

The invention further relates to an expression vector comprising a nucleic acid construct comprising a nucleic acid sequence encoding a polypeptide exhibiting polysaccharide deacetylase activity and having an amino acid sequence which has at least 50% identity with the amino acid sequence of SEQ ID NO:1 as defined in the former section. Preferably, the expression vector comprises said nucleic acid sequence, which is operably linked to one or more control sequences, which direct the production of the encoded polypeptide in a suitable expression host. At a minimum control sequences include a promoter and transcriptional and translational stop signals. The expression vector may be seen as a recombinant expression vector. The expression vector may be any vector (e.g. plasmic, virus), which can be conveniently subjected to recombinant DNA procedures and can bring about the expression of the nucleic acid sequence encoding the polypeptide. Depending on the identity of the host wherein this expression vector will be introduced and on the origin of the nucleic acid sequence of the invention, the skilled person will know how to choose the most suited expression vector and control sequences. Most preferred host cells are presented in the section entitled host cells.

In the context of the invention, an expression vector when introduced into a host cell will lead to a cell having an increased expression level of the nucleic acid sequence present in the expression vector, and/or an increased expression level of the polypeptide encoded by the nucleic acid sequence present in the expression vector and/or an increased activity level of the polypeptide encoded by the nucleic acid sequence present in the expression vector. In this context, the increase is assessed by comparison with the host cell which does not comprise said expression vector and/or with the host cell which does not comprise an endogenous polypeptide having at least 50% identity with SEQ ID NO:1.

In another aspect of the invention, there is provided an expression vector as earlier defined being for use for preparing a medicament. Preferably said medicament is a vaccine or an adjuvant as later defined herein.

Inactivation Vector

The invention further relates to an inactivation vector comprising a nucleic acid construct comprising a nucleic acid sequence encoding a polypeptide exhibiting glycosyltransferase activity and having an amino acid sequence which has at least 50% identity with the amino acid sequence of SEQ ID NO:2 as defined in the former section. An inactivation vector is designed to lower or inactivate the expression of the nucleic acid sequence which has at least 50% identity with the amino acid sequence of SEQ ID NO:2 in a given host.

The inactivation vector may be seen as a recombinant expression vector. The inactivation vector may be any vector (e.g. plasmic, virus), which can be conveniently subjected to recombinant DNA procedures and can bring about the inactivation of the expression of the nucleic acid sequence as defined above. Depending on the identity of the host wherein this inactivation vector will be introduced and on the origin of the nucleic acid sequence of the invention, the skilled person will know how to choose the most suited inactivation vector. Most preferred host cells are presented in the section entitled host cells.

In the context of the invention, an inactivation vector when introduced into a host cell will lead to a cell having a decreased (or lowered) expression level of the nucleic acid sequence present in the expression vector, and/or a decreased expression level of the polypeptide encoded by the nucleic acid sequence present in the expression vector and/or a decreased activity level of the polypeptide encoded by the nucleic acid sequence present in the expression vector. In this context, the decrease is preferably assessed by comparison with the host cell which does not comprise said inactivation vector.

The decrease of the expression level of the polypeptide exhibiting glycosyltransferase activity and having an amino acid sequence which has at least 50% identity with the amino acid sequence of SEQ ID NO:2 and/or the lowering of its activity level may have been achieved by conventional methods known in the art, such as by inactivating or down-regulating the expression of the endogenous nucleic acid sequence encoding said glycosyltransferase in the host. This inactivation or down regulation may have been achieved by deletion of one or more nucleotides in the nucleic acid sequence encoding said polypeptide. In another embodiment, the invention relates to a host, preferably a *Bordetella* which has a mutation in its nucleic acid sequence encoding said glycosyltransferase. Preferably to construct a host having an inactivated nucleic acid sequence encoding a glycosyltransferase, a replacement or inactivation vector is prepared and is subsequently introduced into the host by transformation. The skilled person will know how to construct such a vector.

Alternatively or in combination with the inactivation of the endogenous nucleic acid sequence encoding the glycosyltransferase, the expression of the nucleic acid sequence encoding the glycosyltransferase can be lowered by fusing it to a weak promoter suitable for low level protein expression in the selected organism.

Alternatively or in combination with the inactivation of the nucleic acid sequence encoding the endogenous glycosyltransferase, the expression of the nucleic acid sequence encoding the glycosyltransferase may be rendered inducible by fusing it to an inducible promoter suitable for inducible level protein expression in the selected organism.

Alternatively or in combination with former defined preferred embodiment, the inactivation of the nucleic acid sequence encoding the endogenous glycosyltransferase is preferably achieved by using a suicide vector. More preferably, the suicide vector is pSS1129 (Stibitz et al, 1994).

In another aspect of the invention, there is provided an inactivation vector as earlier defined for use for preparing a medicament. Preferably said medicament is a vaccine or an adjuvant as later defined herein.

Host Cell

In a further aspect, the invention provides a host cell comprising the expression vector of the invention and/or the inactivation vector of the invention both as defined in former sections. The choice of the host cell will to a large extent depend upon the source of the nucleic acid sequence of the invention. Depending on the identity of the host cell, the skilled person would know how to transform it with the construct or vector of the invention.

The host cell may be any microbial, prokaryotic or eukaryotic cell, which is suitable for expression of the LPS of the invention. In a preferred embodiment, the host cell is a *Bordetella* species as earlier mentioned herein. Most preferably, the *Bordetella* is a *Bordetella pertussis.*

Suitable procedures for transformation of *Bordetella* may involve a process comprising conjugation in a manner known to the skilled person. Suitable transformation procedures for *Bordetella* are described in Stibitz et al, 1994.

According to a first preferred embodiment, the host cell hence obtained has an increased expression level of the nucleic acid sequence present in the expression vector, and/or has an increased expression level of the polypeptide encoded by the nucleic acid sequence present in the expression vector and/or has an increased activity level of the polypeptide encoded by the nucleic acid sequence present in the expression vector. In this embodiment, the nucleic acid sequence present in the expression construct codes for a polypeptide having at least 50% identity with SEQ ID NO:1. In this context, the increase is assessed by comparison with the host cell which does not comprise said expression vector and/or with the host cell which does not comprise an endogenous polypeptide having at least 50% identity with SEQ ID NO:1 when both cultured and/or assayed under the same conditions.

"Increase expression level of the polypeptide" is herein preferably defined as producing more of the polypeptide as earlier defined than what the parental host cell the transformed host cell derives from will produce when both types of cells (parental and transformed cells) are cultured under the same conditions. Preferably, the host cell of the invention produces at least 3%, 6%, 10% or 15% more of the polypeptide of the invention having at least 50% identity with SEQ ID NO:1 than the parental host cell the transformed host cell derives from will produce when both types of cells (parental and transformed cells) are cultured under the same conditions. Also hosts which produce at least 20%, 30%, 40%, 50%, 60%, 70%, 80%, 90%, 100% or 150% more of said polypeptide than the parental cell are preferred. According to another preferred embodiment, the production level of this polypeptide of the host cell of the invention is compared to the production level of the B213 *Bordetella pertussis* strain (Kasuga et al 1953, see also Table 1), which is taken as control. According to an even more preferred embodiment, when the host cell of the invention is an *Bordetella pertussis* strain, the production level of the polypeptide of the host cell of the invention is compared to the production level of the B213 strain as defined above, which is taken as control.

The assessment of the production level of the polypeptide may be performed at the mRNA level by carrying out a Northern Blot or an array analysis and/or at the polypeptide level by carrying out a Western blot. All these methods are well known to the skilled person.

"Increase in the polypeptide activity" is herein defined as exhibiting a higher polysaccharide deacetylase activity than the one of the parental host cell the transformed host cell derives from using an assay specific for said activity. Preferably, the assay is the one mentioned under the section polypeptides. Preferably, the host cell of the invention exhibits at least 3%, 6%, 10% or 15% higher polysaccharide deacetylase activity than the parental host cell the transformed host cell derives from will exhibit as assayed using a specific assay for said activity, which is preferably the assay mentioned under the section polypeptides. Also host which exhibits at least 20%, 30%, 40%, 50%, 60%, 70%, 80%, 90%, 100% or 150% more of said activity than the parental cell are preferred. According to another preferred embodiment, the level of polysaccharide deacetylase activity of the host cell of the invention is compared to the corresponding activity of the B213 strain as defined before, which is taken as control.

According to a more preferred embodiment, when the host cell of the invention is an *Bordetella pertussis* strain, the level of polysaccharide deacetylase activity of the host cell of the invention is compared to the corresponding activity of the B213 strain as defined before, which is taken as control.

The increase in polypeptide expression and/or activity may have been achieved by conventional methods known in the art, such as by introducing more copies of the nucleic acid sequence encoding the polysaccharide deacetylase into the host, be it on a carrier or in the chromosome, than naturally present. Alternatively, the nucleic acid sequence encoding the polysaccharide deacetylase can be overexpressed by fusing it to highly expressed or strong promoter suitable for high level protein expression in the selected organism, or combination of the two approaches. The skilled person will know which strong promoter is the most appropriate depending on the identity of the host cell. Preferably when the host cell is a *Bordetella pertussis* strain, the strong promoter is the tac-promoter of the vector pMMB67EH (Methods for General and Molecular Bacteriology, Editors P. Gerhardt et al., American Society for Microbiology, Washington D.C., 1994, p. 409-410).

Alternatively or in combination with first preferred embodiment, the invention provides a second preferred embodiment, wherein the host cell has a decreased expression level of the nucleic acid sequence encoding the polypeptide having at least 50% identity with the amino acid sequence of SEQ ID NO:2, and/or has a decreased expression level of said polypeptide and/or has a decreased activity level of said polypeptide, preferably via the use of the inactivation vector of the invention as earlier defined herein. In this embodiment, the nucleic acid sequence present in the inactivation vector codes for a polypeptide having at least 50% identity with SEQ ID NO:2. In this context, the decrease is assessed by comparison with the host cell which does not comprise said inactivation vector when both cultured and/or assayed under the same conditions.

"Decrease expression level of the polypeptide" is herein preferably defined as producing less of the polypeptide (as earlier defined) than what was produced by the parental host cell from which the transformed host cell was derived when both types of cells (parental and transformed cells) are cultured under the same conditions. Preferably, the host cell of the invention produces at least 3%, 6%, 10% or 15% less of the polypeptide of the invention having at least 50% identity with SEQ ID NO:2 than that produced by the parental host cell from which the transformed host cell was derived when both types of cells (parental and transformed cells) are cultured under the same conditions. Also hosts which produce at least 20%, 30%, 40%, 50%, 60%, 70%, 80%, 90%, 100% or 150% less of said polypeptide than the parental cell are preferred. According to another preferred embodiment, the production level of this polypeptide of the host cell of the invention is compared to the production level of the B213 strain as defined before, which is taken as control. According to an even more preferred embodiment, when the host cell of the invention is a *Bordetella pertussis* strain, the production level of the polypeptide of the host cell of the invention is compared to the production level of the B213 strain as defined before, which is taken as control.

The assessment of the production level of the polypeptide may be performed at the mRNA level by carrying out a Northern Blot or an array analysis and/or at the polypeptide level by carrying out a Western blot. All these methods are well known to the skilled person.

"Decrease in the polypeptide activity" is herein defined as exhibiting a lower glycosyltransferase activity than the one of the parental host cell from which the transformed host cell was derived, using an assay specific for said activity. Preferably, the assay is the one which has been already described herein under the section "Polypeptides." Preferably, the host cell of the invention exhibits at least 3%, 6%, 10% or 15% lower glycosyltransferase activity than that of the parental host cell from which the transformed host cell was derived as assayed using a specific assay for said activity, which is preferably the assay described under the section "Polypeptides." Also hosts which exhibit at least 20%, 30%, 40%, 50%, 60%, 70%, 80%, 90%, 100% or 150% less of said activity than the parental cell are preferred. According to another preferred embodiment, the level of glycosyltransferase activity of the host cell of the invention is compared to the corresponding activity of the B213 strain as defined before, which is taken as control. According to a more preferred embodiment, when the host cell of the invention is a *Bordetella pertussis* strain, the level of polysaccharide deacetylase activity of the host cell of the invention is compared to the corresponding activity of the B213 strain as defined before, which is taken as control.

The decrease in polypeptide expression and/or activity may have been achieved by conventional methods known in the art, such as by introducing more copies of the nucleic acid sequence encoding the polysaccharide deacetylase into the host, be it on a carrier or in the chromosome, than naturally present. Alternatively, the nucleic acid seqeunce encoding the polysaccharide deacetylase can be overexpressed by fusing it to highly expressed or strong promoter suitable for high level protein expression in the selected organism, or combination of the two approaches. The skilled person will know which strong promoter is the most appropriate depending on the identity of the host cell. Preferably when the host cell is a *Bordetella pertussis* strain, the strong promoter is the tac-promoter of the vector pMMB67EH as defined before.

According to a more preferred embodiment, the host cell does not produce any detectable amounts of glycosyltransferase of the invention and/or does not exhibit any detectable glycsosyltransferase activity. Preferably, the host cell does not produce or produces substantially no glycosyltransferase.

Alternatively, according to another more preferred embodiment, the host cell produces an inducible amount of the glycosyltransferase of the invention and/or exhibit an inducible glycosyltransferase activity.

The decreasing of the expression level of the glycosyltransferase of the invention and/or the decreasing of its activity level may have been achieved by conventional methods known in the art, such as by inactivating or down-regulating the nucleic acid sequence encoding the endogenous glycosyltransferase of the host. This inactivation or down regulation may have been achieved by deletion of one or more nucleotides in the encoding gene. In another embodiment, the invention relates to a host, preferably a *Bordetella pertussis* which has a mutation in its nucleic acid sequence encoding the glycosyltransferase. Preferably to construct a host having an inactivated nucleic acid sequence encoding the glycosyltransferase, a replacement or inactivation vector is prepared and is subsequently introduced into the host by transformation. The skilled person will know how to construct such a vector.

Alternatively or in combination with the inactivation of the endogenous nucleic acid sequence, the expression of the nucleic acid sequence encoding the glycosyltransferase can be decreased by fusing it to a weak promoter suitable for low level protein expression in the selected organism.

Alternatively or in combination with the inactivation of the endogenous nucleic acid sequence, the expression of the nucleic acid sequence encoding the glycosyltransferase can be rendered inducible by fusing it to an inducible promoter suitable for inducible level protein expression in the selected organism. Preferably when the host cell is a *Bordetella pertussis* strain, the inducible promoter is the tac-promoter of the vector pMMB67EH as defined before Surprisingly, the host cell of the invention has attractive properties, which renders it very attractive to be used as a whole *pertussis* vaccine or as an adjuvant: improved potentiality to interact with DC, and to subsequently induce their maturation, and induce the production of proinflammatory cytokines. Alternatively or in combination, the LPS obtainable from these cells is also very suited to be used as a vaccine or as an adjuvant as presented below.

Accordingly, in another aspect of the invention, there is provided a host cell as earlier defined for use as a medicament. Preferably said medicament is a vaccine or an adjuvant as later defined herein.

LPS Obtainable by the Host Cell

In a further aspect, the invention relates to the LPS obtainable from the host cell of the invention as earlier defined herein. Preferably, the host cell is a *Bordetella* species, more preferably a *Bordetella pertussis*, even more preferably a *Bordetella pertussis* carrying an overexpression of the polysaccharide deacetylase of the invention and/or an inactivation of the glycosyltransferase of the invention. More preferably, the LPS is of the invention is obtainable from mutant 2331 as prepared in the examples. Even more preferably, when analysed after isolation with hot phenol/water extraction (Westphal and Jann, 1965), O-deacylation by mild hydrolysis (Holst 2000) and analysis by ESI-MS in the negative ion-mode, the ESI-MS spectrum of the LPS of the invention is characterized by giving more ions than the corresponding ESI-MS spectrum of the LPS derived from a wild type *Bordetella pertussis*, named wild type LPS. Preferably the wild type *Bordetella pertussis* is strain B213 as defined before. Without willing to be bound by any theory, these additional ions may reflect at least partly the increased substitution of the 1 or 4' phosphate groups of the lipid A part of LPS with hexosamine residues.

Typically the ESI-MS spectrum of the wild type LPS is characterized by giving 7 ions (see table 3), whereas the ESI-MS spectrum of the LPS of the invention is characterized by giving more than 7 ions, at least 8, at least 10, at least 12 and more preferably 14 ions.

Alternatively or in combination with former embodiment, preferably, the ESI-MS spectrum of the LPS of the invention comprises more ions comprising hexosamine than the ESI-MS spectrum of the wild type LPS. Typically, the ESI-MS spectrum of the wild type LPS gives two ions with hexosamine (see table 3), whereas the ESI-MS spectrum of the LPS of the invention is characterized by giving more than two ions, at least 4, at least 6, and more preferably 8 ions.

Pharmaceutical Compositions and Medical Uses

The invention further relates to a pharmaceutical composition comprising the host cell of the invention and/or the LPS of the invention both as earlier defined herein. The pharmaceutical composition may be used as a vaccine or as an adjuvant. The vaccine may be used for immunisation (raising an immune response) or vaccination of a mammal.

Adjuvants are herein defined to include any substance or compound that, when used in combination with an antigen, to immunise a mammal, preferably a human, stimulates the immune system, thereby provoking, enhancing or facilitating the immune response against the antigen, preferably without generating a specific immune response to the adjuvant itself. Preferred adjuvants enhance the immune response against a given antigen by at least a factor of 1.5, 2, 2.5, 5, 10 or 20, as compared to the immune response generated against the antigen under the same conditions but in the absence of the adjuvant. Tests for determining the statistical average enhancement of the immune response against a given antigen as produced by an adjuvant in a group of animals or humans over a corresponding control group are available in the art. The adjuvant preferably is capable of enhancing the immune response against at least two different antigens. The adjuvant of the invention will usually be a compound that is foreign to a mammal, thereby excluding immunostimulatory compounds that are endogenous to mammals, such as e.g. interleukins, interferons and other hormones.

In a preferred embodiment, when the pharmaceutical composition is used as an adjuvant, the composition further comprises an antigen.

When the composition is used as a vaccine, the antigen is present at the surface of the host cell of the invention and/or is present within the LPS obtainable from such cells. In this case the vaccine is preferably a vaccine against the host of the invention and/or against any host capable of expressing a related LPS molecule.

When the composition is used as an adjuvant, preferably an antigen is present. The antigen is preferably an antigen from or produced by a bacterium, a virus, a fungus, a parasite, a cancer cell or an allergen as further defined below. The antigen and the host cell of the invention and/or the LPS obtainable by such cells are preferably used in the treatment and/or prevention of an infectious disease caused by the bacterium, virus, fungus, or parasite, or the tumor caused by the cancer cell, or the allergy caused by the allergen.

In a further preferred embodiment, the pharmaceutical composition comprising a host cell of the invention and/or a LPS obtainable therefrom and optionally an antigen as herein defined above further comprises a pharmaceutically acceptable carrier. The pharmaceutical compositions may further comprise pharmaceutically acceptable stabilizing agents, osmotic agents, buffering agents, dispersing agents, and the like. The preferred form of the pharmaceutical composition depends on the intended mode of administration and therapeutic application. The pharmaceutical carrier can be any compatible, non-toxic substance suitable to deliver the active ingredients, i.e. the host cell of the invention and/or the LPS obtainable from this host cell and optionally the antigen, to the patient. Pharmaceutically acceptable carriers for intranasal delivery are exemplified by water, buffered saline solutions, glycerin, polysorbate 20, cremophor EL, and an aqueous mixture of caprylic/capric glyceride, and may be buffered to provide a neutral pH environment. Pharmaceutically acceptable carriers for parenteral delivery are exemplified by sterile buffered 0.9% NaCl or 5% glucose optionally supplemented with a 20% albumin. Preparations for parental administration must be sterile. The parental route for administration of the active ingredients is in accord with known methods, e.g. injection or infusion by subcutaneous, intravenous, intraperitoneal, intramuscular, intraarterial or intralesional routes. The compositions of the invention are preferably administered by bolus injection. A typical pharmaceutical composition for intramuscular injection would be made up to contain, for example, 1-10 ml of phosphate buffered saline and 1 to 100 μg, preferably 15-45 μg of antigen and 1 to 100 μg, preferably 15-45 μg of the host cell and/or LPS of the invention. For oral administration, the active ingredient can be administered in liquid dosage forms, such as elixirs, syrups, and suspensions. Liquid dosage forms for oral administration can contain coloring and flavoring to increase patient acceptance. Methods for preparing parenterally, orally or intranasally administrable compositions are well known in the art and described in more detail in various sources, including, for example, Remington's Pharmaceutical Science (15th ed., Mack Publishing, Easton, Pa., 1980) (incorporated by reference in its entirety for all purposes).

The antigen in the composition of the invention preferably is an antigen that is from or produced by a bacterium, a virus, a fungus, a parasite, a cancer cell or an allergen. Viral antigens that may be combined with the host cell and/or LPS of the invention can be derived from all sorts of viruses, non-limiting examples of such viruses are: Retroviridae such as Human Immunodeficiency virus (HIV); a rubellavirus; paramyxoviridae such as parainfluenza viruses, measles, mumps, respiratory syncytial virus, human metapneumovirus; flaviviridae such as yellow fever virus, dengue virus, Hepatitis C Virus (HCV), Japanese Encephalitis Virus (JEV), tick-borne encephalitis, St. Louis encephalitis or West Nile virus; Herpesviridae such as Herpes Simplex virus, cytomegalovirus, Epstein-Barr virus; Bunyaviridae; Arenaviridae; Hantaviridae such as Hantaan; Coronaviridae; Papovaviridae such as human Papillomavirus; Rhabdoviridae such as rabies virus. Coronaviridae such as human coronavirus; Alphaviridae, Arteriviridae, filoviridae such as Ebolavirus, Arenaviridae, poxyiridae such as smallpox virus, and African swine fever virus. Likewise the host cell and/or LPS of the invention may be combined with antigens derived from pathogenic bacteria, fungi (including yeasts), or parasites. Such antigens include bacterial antigens of e.g. *Helicobacter*, such as *H. pylori, Neisseria*, such as *N. mengitidis, Haemophilus*, such as *H. influenza, Bordetella*, such as *B. pertussis, Chlamydia, Streptococcus*, such as *Streptococcus* sp. serotype A, *Vibrio*, such as *V. cholera*, Gram-negative enteric pathogens including e.g. *Salmonella, Shigella, Campylobacter* and *Escherichia*, as well as antigen from bacteria causing anthrax, leprosy, tuberculosis, diphtheria, Lyme disease, syphilis, typhoid fever, and gonorrhea. Antigens from parasites e.g. include antigens from protozoans, such as *Babeosis bovis, Plasmodium, Leishmania* spp. *Toxoplasma gondii*, and *Trypanosoma*, such as *T. cruzi*. Fungal antigens may include antigens from fungi such as *Aspergillus* sp., *Candida albicans, Cryptococcus*, such as e.g *C. neoformans*, and *Histoplasma capsulatum*.

Although vaccination is generally applied for the prophylactic protection against pathogens or for the treatment of diseases following pathogenic infection, the person skilled in the art is aware of the application of vaccines for tumor-treatment. Moreover, an increasing number of tumor-specific proteins are found to be proper entities that can be targeted by human or humanized antibodies. Such tumor-specific proteins are also within the scope of the present invention. Many tumor specific antigens are known in the art. Therefore, in one preferred embodiment, the invention provides compositions comprising a tumor-specific antigen and a host cell and/or LPS as defined above. Suitable tumor antigens include e.g. carcinoembryonic antigen, prostate-specific membrane antigen, prostate specific antigen, protein MZ2-E, polymorphic epithelial mucin (PEM), folate-binding-protein LK26, (truncated) epidermal growth factor receptor (EGRF), HER2, Thomsen-Friedenreich (T) antigen, GM-2 and GD-2 gangliosides, Ep-CAM, mucin-1, epithialial glycoprotein-2, and colon specific antigen.

In addition, antigens can be targeted to DC's in order to induce tolerance in the prevention of auto-immune disease. Such allergens are also within the scope of the present invention.

Accordingly, in a further aspect, the host cell of the invention, preferably a *Bordetella pertussis* and/or the LPS obtainable from such cell is/are for use as a medicine. Preferably, the medicine is a vaccine against *pertussis*.

In another preferred embodiment, the host cell of the invention, preferably a *Bordetella pertussis* and/or the LPS obtainable from such cell is/are for use as an adjuvant. More preferably, the host cell of the invention, preferably a *Bordetella pertussis* and/or the LPS obtainable from such cell are used in combination with an antigen.

Accordingly in a further aspect, the invention relates to the use of the host cell of the invention, preferably a *Bordetella pertussis* and/or the LPS obtainable from such cell for the preparation of a medicament for the prevention and/or treatment of *pertussis*. In a preferred embodiment, the host cell of the invention, preferably a *Bordetella pertussis* and/or the LPS obtainable from such cell are used as adjuvant for the preparation of a medicament for raising an immune response against an antigen. More preferably, the host cell of the invention and/or the LPS obtainable from such cell are used as adjuvant in combination with said antigen.

Accordingly in a further aspect, the invention relates to the use of a polypeptide of the invention as earlier defined herein and/or a nucleic acid sequence of the invention as defined herein for the preparation of a medicament for the prevention and/or treatment of *pertussis*.

Accordingly in a further aspect, the invention relates to the use of a polypeptide of the invention as earlier defined herein and/or a nucleic acid sequence of the invention as earlier defined herein for the preparation of an adjuvant. Preferably, in this aspect, the polypeptide of the invention as earlier defined herein and/or the nucleic acid sequence of the invention as earlier defined herein are used in combination with an antigen for the preparation of a medicament for raising an immune response against the antigen.

In the methods and uses of the invention, the mammal is preferably a human.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

EXAMPLES

Materials and Methods

Bacterial Strains and Growth Conditions

Figure 1:
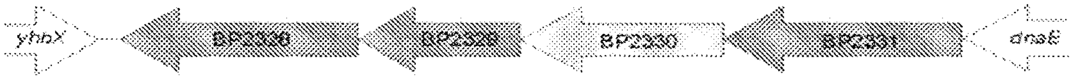
FIG. 1. (A) Schematic representation of the identified glycosyltransferase operon. Dark gray arrows indicate the genes that encode putative glycosyltransferases, whereas the light grey and white arrows indicate the gene encoding a putative monosaccharide deacetylase and the flanking ORFs, respectively. (B) Analysis of LPS profiles from the wild-type *B. pertussis* strain (WT), and the BP2329-, BP2328-, and BP2331-mutant strains by Tricine-SDS-PAGE.
Figure 1:
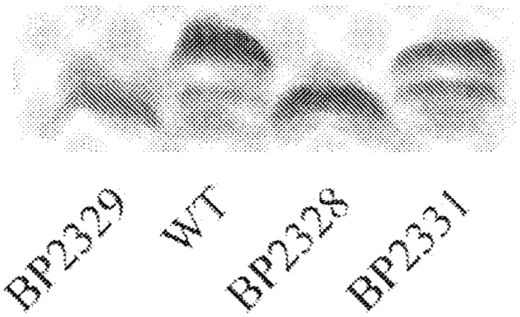

All bacterial strains used are described in Table 1. Typically, the *E. coli* strains were grown at 37° C. in Luria-Bertani broth while shaking at 200 rpm. When appropriate, bacteria were grown in the presence of 100 μg/ml ampicillin, 50 μg/ml kanamycin, or 10 μg/ml gentamicin, for plasmid maintenance or strain selection. *B. pertussis* was grown at 35° C. on Bordet-Gengou (BG) agar supplemented with 15% defibrinated sheep blood (Tritium).

Recombinant DNA Techniques

All plasmids used are described in Table 1. Plasmid DNA was isolated using the Promega Wizard®Plus SV Minipreps system. Restriction endonucleases were used according to the instructions of the manufacturer (Roche). DNA fragments were isolated from agarose gels using the Promega Wizard® SV Gel and PCR Clean-Up system. Ligations were performed using the rapid DNA ligation kit (Roche).

All primers used are described in Table 2. Chromosomal template DNA for PCR reactions was prepared by resuspending ~$10^9$ bacteria in 50 μl of distilled water, after which the suspension was heated for 15 min at 95° C. The suspension was then centrifuged for 1 min at 16,100×g, after which the supernatant was used as template DNA. To construct *B. pertussis* mutant strains B213ΔBP2328 and ΔBP2329, we amplified DNA segments encompassing the 5' region and upstream sequences of the corresponding ORFs by using primers BP2328_FW$_{up}$, BP2329_FW$_{up}$, and primers BP2328_REV$_{up}$ and BP2329_REV$_{up}$, which both contained a BamHI site. Additionally, DNA fragments containing the 3' regions and downstream sequences of the ORFs were obtained by PCR with primers BP2328_FW$_{down}$, BP2329_FW$_{down}$, both containing a BamHI site, and primers BP2328_REV$_{down}$ and BP2329_REV$_{up}$. To construct a *B. pertussis* BP2331 mutant strain, the corresponding ORF was amplified by using primers BP2331_FW and BP2331_REV. The PCRs were performed using pure Taq Ready-to-go PCR beads (Amersham Biosciences) in a 25-μl total reaction volume with 5 pmol of each primer. The temperature program was as follows: 95° C. for 3 min, 30 cycles of 15 s at 95° C., 30 s at 55° C., and 1 min at 72° C., followed by 7 min at 72° C. and subsequent cooling to 4° C. The PCR products were purified from agarose gel and subsequently cloned into pGEM-T Easy resulting in plasmids pGEM-BP2328$_{up}$, pGEM-BP2328$_{down}$, pGEM-BP2329$_{up}$, pGEM-BP2329$_{down}$, and pGEM-BP2331, respectively. The BamHI-SpeI fragments of pGEM-BP2328$_{down}$ and pGEM-BP2329$_{down}$ were ligated into BamHI-SpeI-restricted pGEM-BP2328$_{up}$ and pGEM-BP2329$_{up}$, respectively. The resulting plasmids and plasmid pGEM-BP2331 were cut with BamHI and EcoRV, respectively, to allow for insertion of the kanamycin-resistance cassette from plasmid pBSL128 obtained by BamHI and HindIII digestion, respectively. Finally, EcoRI fragments of the constructs obtained were ligated into the EcoRI-restricted suicide plasmid pSS1129. The final constructs, designated pSS1129-BP2328$_{KO}$, pSS1129-BP2329$_{KO}$, and pSS1129-BP2331$_{KO}$, respectively, contained the kanamycin-resistance cassette in the same orientation as the transcription direction of the operon. The pSS1129-based plasmids were used to transform *E. coli* SM10(λpir), which allowed for subsequent transfer of the plasmids to *B. pertussis* and construction of *B. pertussis* BP2328, BP2329, and BP2331 mutants by allelic exchange. Transformants were screened by PCR using various primer sets.

LPS Isolation and Preparation of De-O-Acylated LPS

LPS was isolated using the hot phenol/water extraction method (Westphal and Jann, 1965) with slight modifications (Geurtsen et al., 2006). De-O-acylation of LPS was achieved by mild hydrazinolysis (Hoist, 2000). Briefly, LPS was dissolved in anhydrous hydrazine (200 μl), and incubated at 37° C. for 50 min with constant stirring to release the O-linked fatty acyl chains. The mixture was cooled and 600 μl of cold acetone were added in small portions to convert hydrazine to acetone hydrazone. The precipitate of the de-O-acylated LPS was collected by centrifugation (4000×g, at 7° C. for 30 min). The pellet was washed twice with 600 μl of cold acetone, centrifuged and dissolved in water before lyophilisation.

Capillary Electrophoresis-Electrospray Mass Spectrometry

A Prince CE system (Prince Technologies) was coupled to a 4000 QTRAP mass spectrometer (Applied Biosystems/MDS Sciex). A sheath solution (isopropanol-methanol, 2:1) was delivered at a flow rate of 1.0 μl/min. Separations were obtained on a ~90-cm length bare fused-silica capillary using 15 mM ammonium acetate in deionised water, pH 9.0. The 5 kV and −5 kV of electrospray ionisation voltage were used for positive and negative ion mode detections, respectively. For all the mass spectrometric experiments, nitrogen was used as curtain and collision gas. In the $MS^2$ (enhanced product ion scan or EPI) and $MS^3$ experiments, the scan speed was set to 4000 Da/s with $Q_0$ trapping, the trap fill time was set as "dynamic" and the resolution of Q1 was set as "unit". For $MS^3$ experiments, the excitation coefficient was set at a value to excite only the first isotope for a single charged precursor with excitation time set at 100 ms.

LPS Analysis by Tricine-SDS-PAGE

Approximately $10^9$ bacteria were suspended in 50 μl of sample buffer (Laemmli, 1970), and 0.5 mg/ml proteinase K (end concentration) was added. The samples were incubated for 60 min at 55° C., followed by 10 min at 95° C. to inactivate proteinase K. The samples were then diluted 10 fold by adding sample buffer, after which 2 μl of each sample were applied to a Tricine-SDS-PAGE gel (Lesse et al., 1990). The bromophenol blue was allowed to run into the separating gel at 35 V, after which the voltage was increased to 105 V. After the front reached the bottom of the gel, electrophoresis was continued for another 45 min. The gels were fixed overnight in water/ethanol/acetic acid 11:8:1 (v/v/v) and subsequently stained with silver as described (Tsai and Frasch, 1982).

Preparation of Bacterial Cell Suspensions

Bacteria were inactivated in 0.5% paraformaldehyde (PFA) in phosphate-buffered saline (PBS) for 30 min and washed thoroughly in RPMI 1640 medium without phenol red (Gibco). Bacterial suspensions with an optical density at 600 nm ($OD_{600}$) of 1, corresponding to ~$10^9$ bacteria/ml, were prepared in RPMI 1640 medium without phenol red.

Human DC Generation and Culture

Immature human DC were generated from human peripheral blood mononuclear cells (PBMCs) as described previously with minor modifications (Sallusto and Lanzavecchia, 1994). Briefly, PBMCs were isolated from heparinised blood from healthy volunteers using density-gradient centrifugation over a FICOLL® gradient (Amersham Biosciences). Recovered PBMC fractions were washed three times in RPMI 1640 medium, supplemented with 10% heat-inactivated fetal calf serum (FCS) (Bodinco BV). Next, monocytes were prepared from PBMCs by centrifugation over a three-layer PERCOLL® gradient (GE Healthcare Bio-Sciences AB) (60%, 47.5%, and 34% Percoll in RPMI 1640, 10% FCS). Monocytes were harvested from the upper interface and washed three times with RPMI 1640, 10% FCS medium and incubated in a six-well plate (4 ml per well, $0.5\times10^6$ cells/ml) in RPMI 1640, 10% FCS, supplemented with 2.4 mM L-glutamine (Sigma-Aldrich), 100 U/ml penicillin-streptomycin (Gibco), 100 ng/ml of human recombinant GM-CSF (Peprotech), and 50 ng/ml of human recombinant IL-4 (Strathmann-Biotec AG). After six days of culture, immature DC (imDC) were harvested, which were negative for CD14 and CD83, expressed low levels of CD86 and HLA-DR, and expressed high levels of CD40 and CD11c as assessed by flow cytometry.

DC Stimulation

ImDC were washed and resuspended at a concentration of $5\times10^5$ cells/ml in RPMI 1640 10% FCS, and co-incubated with either PFA-fixed *B. pertussis* cells at a multiplicity of infection (MOI) of 10 or 100, or purified LPS at a concentration of 10 or 1000 ng/ml. Unstimulated imDC served as control in all experiments. DC were harvested after 24 h and directly stained for expression of cell surface markers; the supernatants were stored at −80° C. before cytokine measurements.

Flow Cytometric Analysis of Cell Surface Markers

Surface expression of DC maturation markers and co-stimulatory molecules was assessed by flow cytometry. Immature or stimulated DC were harvested, washed in RPMI 1640, 10% FCS and resuspended in filter-sterilised PBS containing 0.1% bovine serum albumin (FACS buffer). Next, cells were incubated for 30 min at 4° C. with either one of the following antibodies: FITC-conjugated anti-human CD11c (mIgG1) and CD83 (mIgG1), phycoerythrin-conjugated anti-human CD86 (mIgG1) and CD40 (mIgG1), allophycocyanin-conjugated anti-human CD14 (mIgG1) and HLA-DR (mIgG2b) and appropriate fluorochrome-labelled isotype controls (CD11c, CD40 and CD14 from eBioscience; CD83, CD86 and HLA-DR from BD Pharmingen). Cells were washed twice with FACS buffer and analysed using flow cytometry (FACScan, Becton Dickinson).

Cytokine Measurements

Human IL-10 and IL-12p70 concentrations in the supernatants of stimulated DCs were determined using an Enzyme-linked Immunosorbent Assay (ELISA) according to the manufacturer's instructions (BD Biosciences Pharmingen).

Endotoxic Activity Assays

The human macrophage cell line MM6 (Ziegler-Heitbrock et al., 1988) was stimulated with serial dilutions of whole bacterial cell suspensions or purified LPS as described (Geurtsen et al., 2006). The bacterial cell suspensions were prepared by collecting the cells from cultures by centrifugation, after which they were resuspended in PBS at an $OD_{590}$ of 1.0, heat-inactivated for 10 min in the presence of 8 mM formaldehyde, and stored at 4° C. Following stimulation, IL-6 concentrations in the culture supernatants were quantified with an ELISA against human IL-6 according to the manufacturer's instructions (PeliKine Compact™)

Results

Identification of a Novel LPS-Biosynthesis Operon in *B. pertussis*

We found a cluster of four genes (BP2328 to BP2331, GenBank Accession Numbers NP_880966 to NP_880969) three of which showed high sequence similarity to LPS glycosyltransferases from various bacteria, i.e., BP2328, BP2329 and BP2331. BP2330 shows the highest similarity to a polysaccharide deacetylase from *Xylella fastidiosa*. The four ORFs are close to each other and in some cases even overlap, suggesting that they constitute an operon (FIG. 1A). The genes upstream and, in the reverse orientation, downstream of the operon, putatively encode homologues of the DNA polymerase III subunit alpha DnaE and of the putative sulfatase YhbX of *E. coli*, respectively. In order to study the role of the putative LPS glycosyltransferases, we made constructs in suicide plasmid pSS1129 carrying the individual BP2328, BP2329, and BP2331 genes interrupted by a kanamycin-resistance cassette for insertional inactivation by allelic exchange. Using this approach, knockout mutants for all three genes could be readily obtained in *B. pertussis* strain B213. Analysis of their LPS by Tricine-SDS-PAGE of whole-cell lysates showed clearly truncated LPS for the BP2328 and BP2329 mutants (FIG. 1B). In contrast, the LPS of the BP2331 mutant strain was more heterogenic and consisted of multiple bands, including the wild-type length.

LPS Structural Analysis

Figure 2:
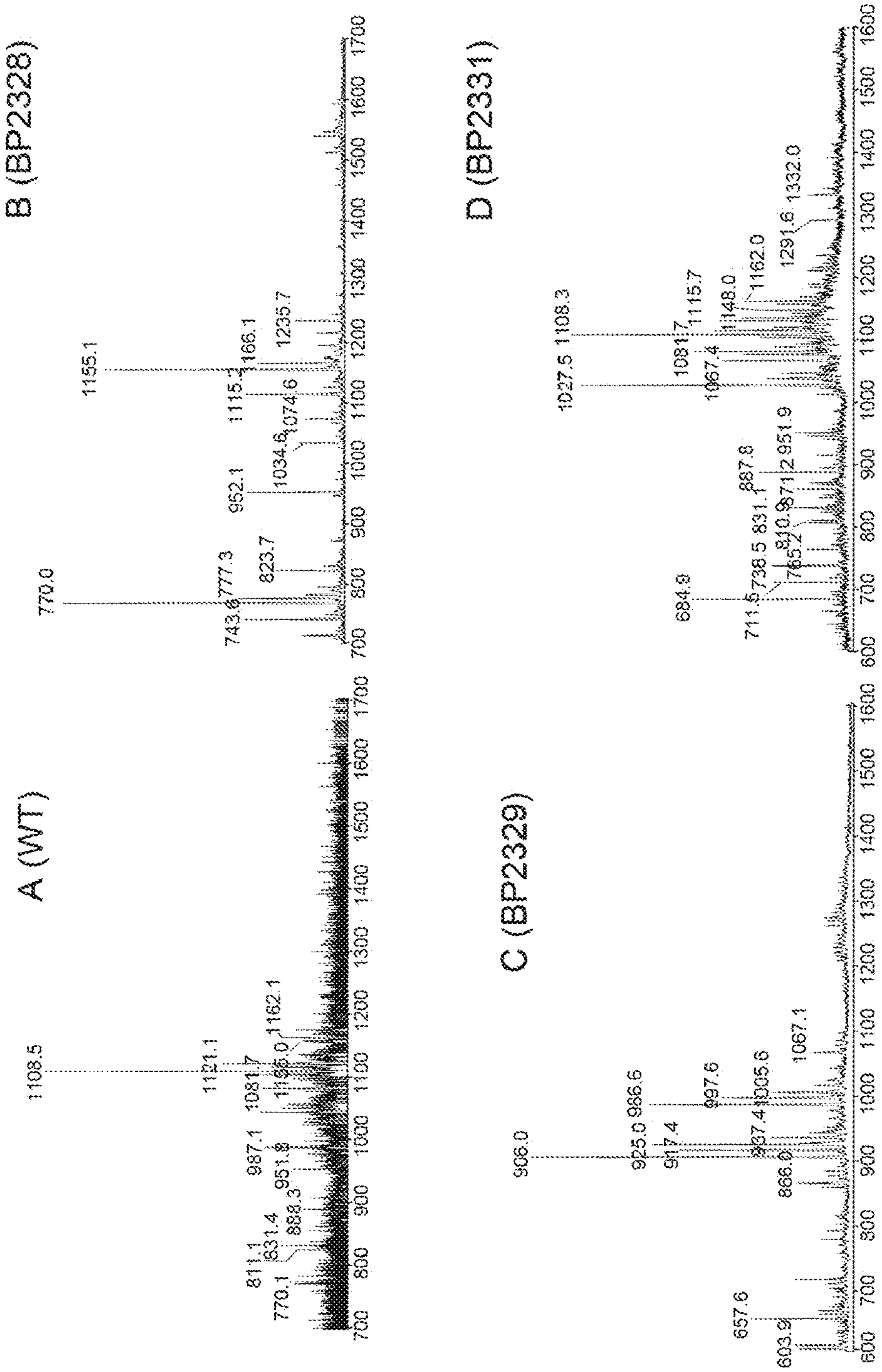
FIG. 2. Negative ion ESI-MS of O-deacylated LPS of wild-type *B. pertussis* (A) and *B. pertussis* mutant strains BP2328 (B), BP2329 (C) and BP2331 (D).

To determine their structure, LPS from the wild-type and BP2328-, BP2329-, and BP2331-mutant strains was isolated, O-deacylated, and analysed by ESI-MS in the negative-ion mode (FIG. 2). The proposed LPS compositions are summarised in Table 3. The spectrum of wild-type LPS (FIG. 2A) revealed a major triply-charged ion at m/z 1108.5 corresponding to full-length *B. pertussis* LPS with the composition GlcNAco•Man2NAc3NAcA•Fuc2NAc4NMe•GalNA•Glc•$GlcN_2$•GlcA•$Hep_3$•P•Kdo•lipid A-OH. Additional ions were present at m/z 770.1 ($[M-3H]^{3-}$), 811.1 ($[M-4H]^{4-}$), 831.4 ($[M-4H]^{4-}$), 888.3 ($[M-3H]^{3-}$), 951.8 ($[M-H]^{-}$), 987.1 ($[M-2H]^{2-}$), 1081.7 ($[M-3H]^{3-}$), 1121.1 ($[M-3H+K]^{3-}$), 1155.0 ($[M-2H]^{2-}$), and 1162.1 ($[M-3H]^{3-}$). Most of these ions corresponded to dephosphorylated or truncated glycoforms; however, the triply-charged ion at m/z 1162.1 corresponded to full-length *B. pertussis* LPS substituted with an additional hexosamine moiety (Table 3). The ESI-MS spectrum of the BP2328-mutant LPS (FIG. 2B) showed triply-charged ions at m/z 743.6, 770.0 and 823.7, together with their corresponding doubly-charged ions at m/z. 1115.2, 1155.1, and 1235.7. Additional peaks were present at m/z 777.3 ($[M-3H+Na]^{3-}$), 952.1 ($[M-H]^{-}$), 1034.6 ($[M-2H]^{2-}$), 1074.6 ($[M-2H]^{2-}$), and 1166.1 ($[M-2H+Na]^{2-}$). Assignment of the peaks revealed that the most complete core OS structure was represented by the ions at m/z 823.7 and 1235.7 corresponding to the composition GalNA•Glc•$GlcN_2$• GlcA•$Hep_2$•P•Kdo•lipid A-OH. BP2329 mutant LPS (FIG. 2C) showed triply charged ions at 603.9 and 657.6, together with their corresponding doubly-charged ions at m/z 906.0 and 986.6. In addition, sodium and potassium adducts of these ions were present at m/z 917.4 and 997.6, and m/z 925.0 and 1005.6, respectively. Additional peaks were present at m/z 866.0 ($[M-2H]^{2-}$), 937.4 ($[M-2H—H_2O]^{2-}$), and 1067.1 ($[M-2H]^{2-}$). In this case, the most complete core structure was represented by the doubly-charged ion at m/z 1067.1 corresponding to the composition $GlcN_2$•GlcA• $Hep_2$•P•Kdo•lipid A-OH, BP2331 mutant LPS (FIG. 2D) showed a large number of peaks, including triply-charged ions at m/z 1108.3 and 1162.0 corresponding to full-length *B. pertussis* LPS and full-length *B. pertussis* LPS substituted with an additional hexosamine, respectively.

Figure 3:
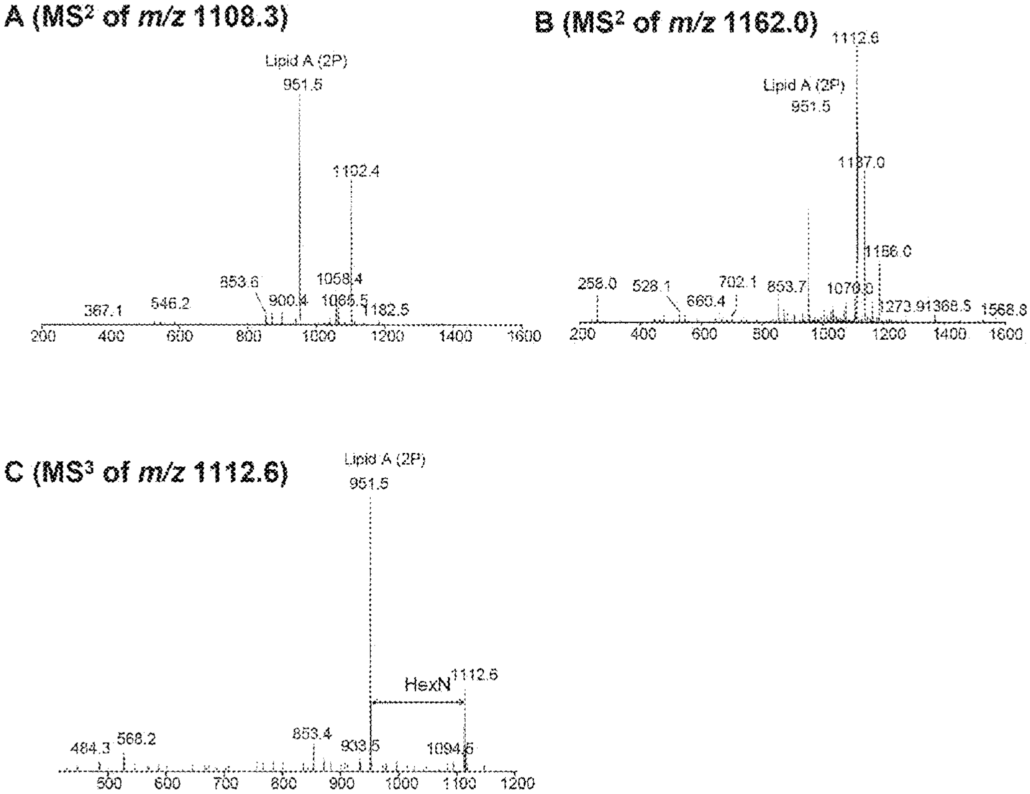
FIG. 3. Negative mode tandem mass spectrometric analysis of O-deacylated LPS from the BP2331-mutant strain. (A) extracted MS/MS spectrum of the ion at m/z 1108.3, (B) extracted MS/MS spectrum of the ion at m/z 1162.0, (C) extracted $MS^3$ spectrum of the ion at m/z 1112.6 from the ion at m/z 1162.0.

To resolve the location of the additional hexosamine moiety, which was observed in both wild-type and BP2331-mutant LPS, ESI-$MS^2$ studies were performed in negative-ion mode (FIG. 3). MS/MS spectra of the ions at m/z 1108.3 (FIG. 3A) and 1162.0 (FIG. 3B) both showed a singly charged fragment ion at m/z 951.5, which revealed that lipid A-OH, resulting from the cleavage between the Kdo-lipid A bond under collision-induced dissociation, consisted of a β-(1→6)-linked disaccharide of N-acylated (3OH C14) glucosamine residues, each residue being substituted with a phosphate group. The spectrum of ion at m/z 1162.0 also showed an additional ion at m/z 1112.6, which indicates that the extra hexosamine residue was directly attached to lipid A. $MS^3$ on m/z 1112.6 further supported this conclusion (FIG. 3C).

Dendritic Cell Activation by *B. pertussis* LPS Mutants

Figure 4A:
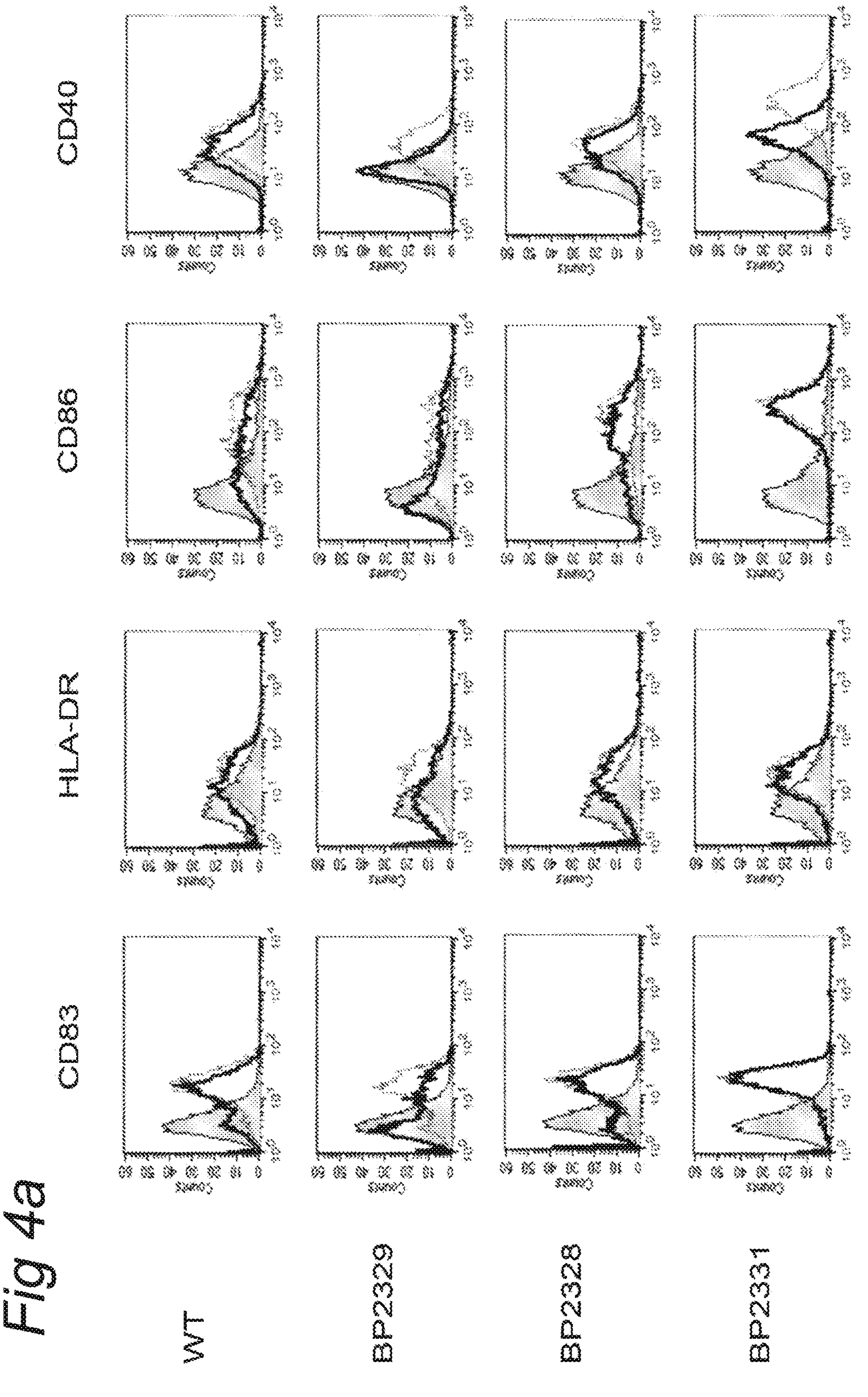
FIG. 4. DC activation after stimulation with the wild-type and mutant *B. pertussis* cells. (A) Analysis of CD83, HLA-DR, CD86, and CD40 cell-surface expression in human DCs after 24 h stimulation with PFA-fixed wild-type and mutant *B. pertussis* cells at MOI 10 (black line) or 100 (dashed line). Unstimulated DCs served as control (grey-filled histogram). Shown are FACS histograms for the indicated *B. pertussis* strains from 5,000 events counted. The vertical axis represents the cell number, while the horizontal axis represents the intensity of staining (B) IL-10 and IL-12p70 production by cultured human DCs after stimulation with PFA-fixed wild-type and mutant *B. pertussis* cells at MOI 10 or 100. Results are expressed as mean cytokine concentrations (±SD).
Figure 4:
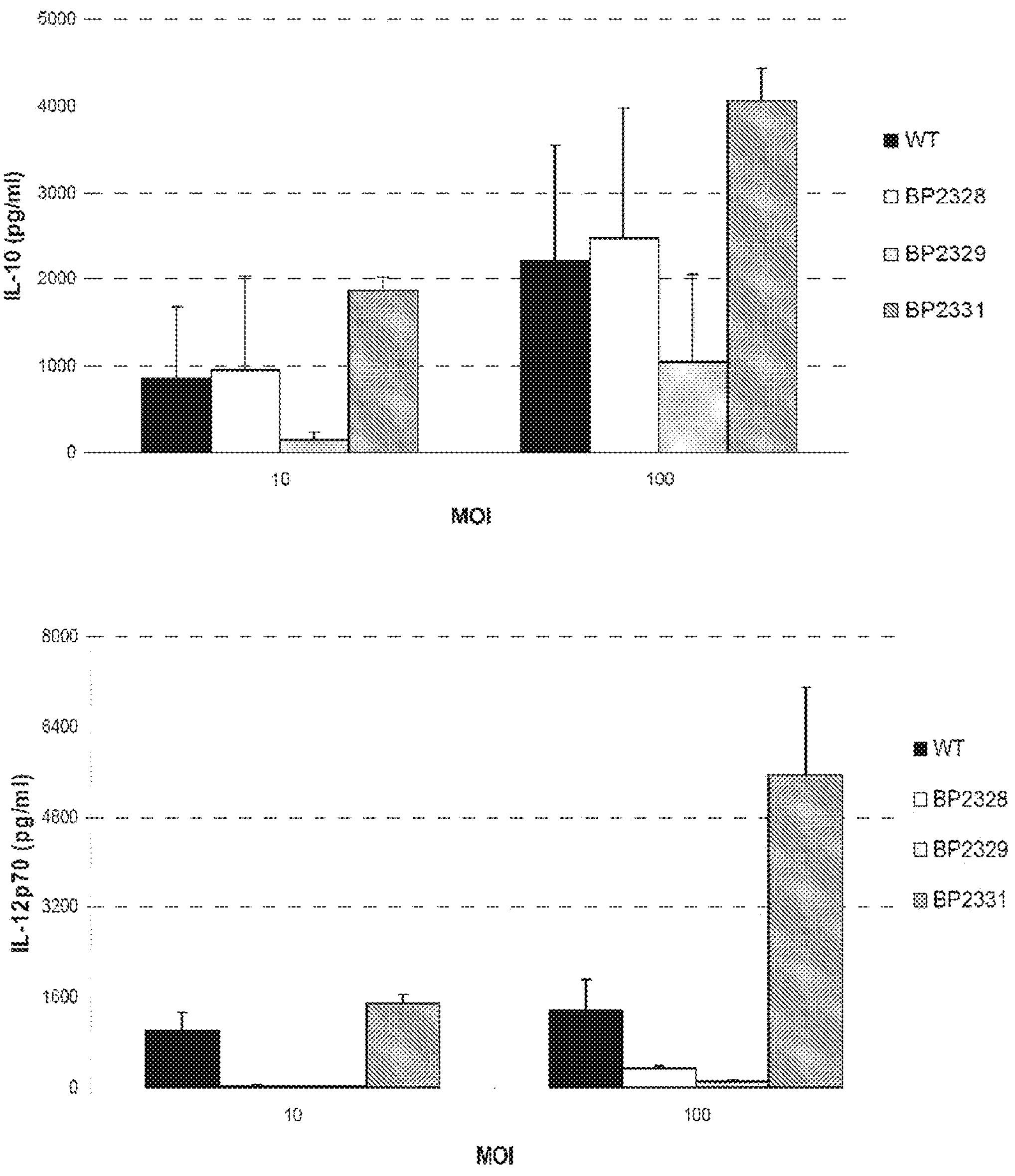

To determine the influence of the LPS mutations on DC activation, immature DCs were co-cultured with PFA-fixed *B. pertussis* wild-type and mutant bacteria at an MOI of 10 and 100. DC activation was monitored by analysis of maturation marker (CD83 and HLA-DR) and co-stimulatory molecule (CD86 and CD40) expression by flow cytometry (FIG. 4A) and IL-10 and IL12p70 induction by ELISA (FIG. 4B). Wild-type and all mutant bacteria induced CD83, HLA-DR, CD86, and CD40 expression, demonstrating that all strains were capable of activating DCs. However, the BP2329- and BP2331-mutant bacteria were clearly less and more stimulatory, respectively, than the wild-type bacteria, whereas the BP2328-mutant strain was as efficient as the wild type. The lower DC maturation observed in the case of the BP2329-mutant strain was accompanied by lower induction of IL-10 and IL-12p70 (FIG. 4B). Similarly, the BP2331 mutant, which displayed an enhanced DC-maturation capacity, induced higher amounts of IL-10 and IL-12p70. The wild-type strain and the BP2328-mutant strain induced comparable levels of IL-10, which is in agreement with the equal expression of co-stimulatory molecules and maturation markers on the DCs in response to these strains. However, whereas the wild-type strain clearly induced IL-12p70 production, this was hardly the case for the BP2328-mutant strain (FIG. 4B), suggesting that IL-10 and IL-12p70 expression can be differentially regulated.

Figure 5:
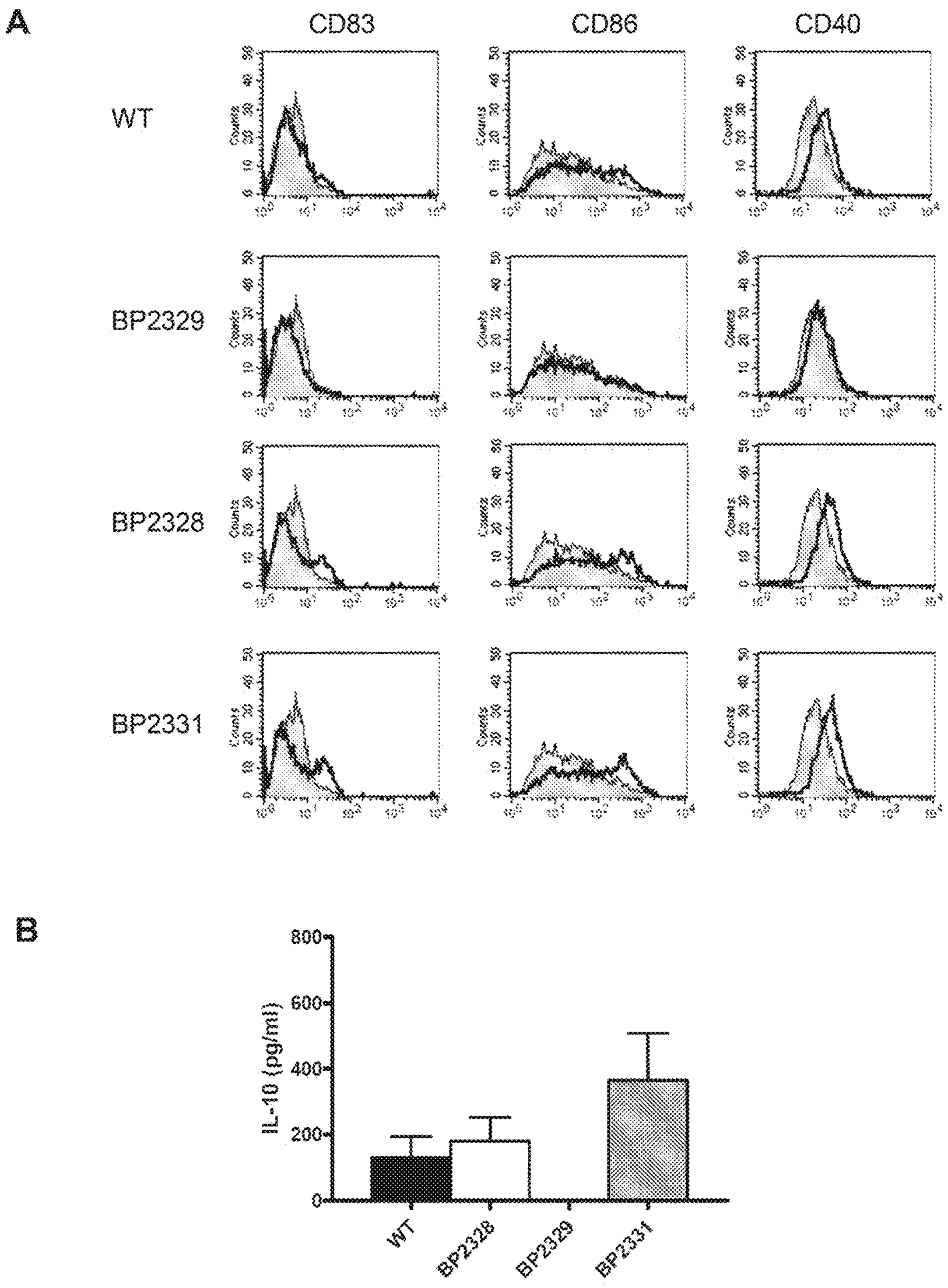
FIG. 5. DC activation after stimulation with purified wild-type and mutant *B. pertussis* LPS. (A) Analysis of CD83, CD86, and CD40 cell-surface expression in human DCs after 24 h stimulation with 1 μg/ml purified LPS. Unstimulated DCs served as control (grey-filled histogram). Shown are FACS histograms for the LPS of the indicated *B. pertussis* strains from 5,000 events counted. The vertical axis represents the cell number, while the horizontal axis represents the intensity of staining (B) IL-10 production by cultured human DCs after stimulation with 1 μg/ml purified LPS. Results are expressed as mean cytokine concentrations.

To assess whether the observed differences in DC activation capacity between the wild-type and mutant strains are directly related to the differences in the LPS composition, DC activation studies were performed with 10 and 1000 ng/ml of purified LPS. In contrast to the high increase in expression of maturation markers and co-stimulatory molecules on DCs in response to wild-type, BP2328-, and BP2331-mutant bacteria, only minor increases in CD83, CD86, and CD40 expression (FIG. 5A) and no increase in HLA-DR expression (data not shown) was found even with 1000 ng/ml LPS of these strains. Similarly, IL-10 induction was low (FIG. 5B) and IL-12p70 could not be detected in supernatants of DCs stimulated with LPS (data not shown). Nevertheless, mutual comparison (FIGS. 5A and 5B) demonstrated that, in accordance with the results obtained with intact bacteria, the highest DC activation capacity was found for the LPS isolated from the BP2331-mutant strain, followed by those of the BP2328-mutant strain and the wild-type strain, whereas that of the BP2329-mutant strain was incapable of maturing DCs. Thus, the alterations in the LPS structure of the mutants differentially affect DC activation capacity.

Endotoxic Activity of LPS and Whole Bacterial Cells

Figure 6:
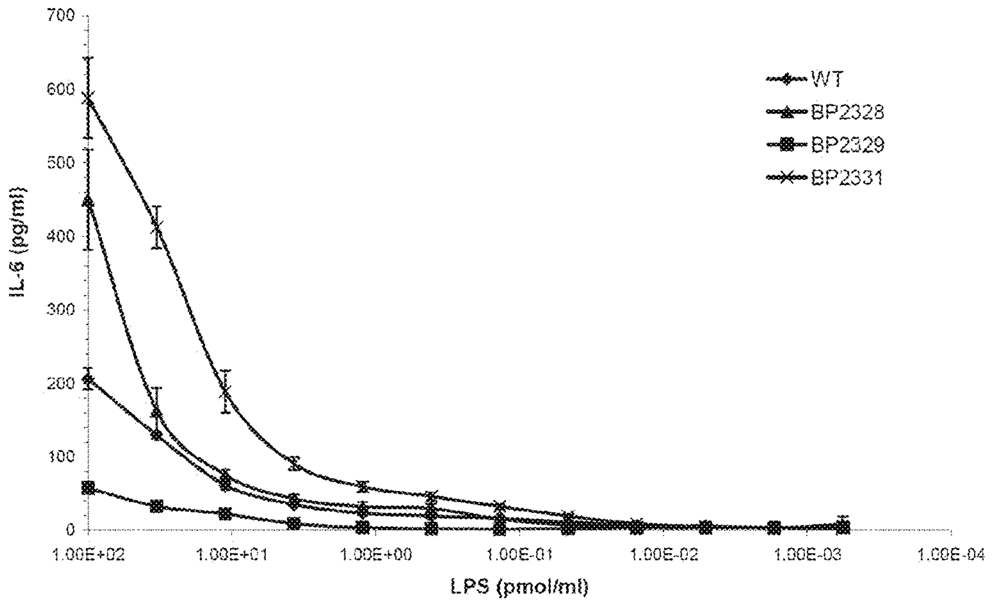
FIG. 6. IL-6 induction by purified *B. pertussis* LPS and whole bacterial cells. The production of IL-6 by the human macrophage cell line MM6 was stimulated with serial dilutions of stock solutions of purified LPS (A) or whole bacterial cells (B) from the wild-type *B. pertussis* strain (WT), or the BP2328-, BP2329-, and BP2331-mutant strains. IL-6 concentrations in the culture supernatants were quantified in an ELISA against human IL-6. The data represent the averages of three individual experiments.
Figure 6:
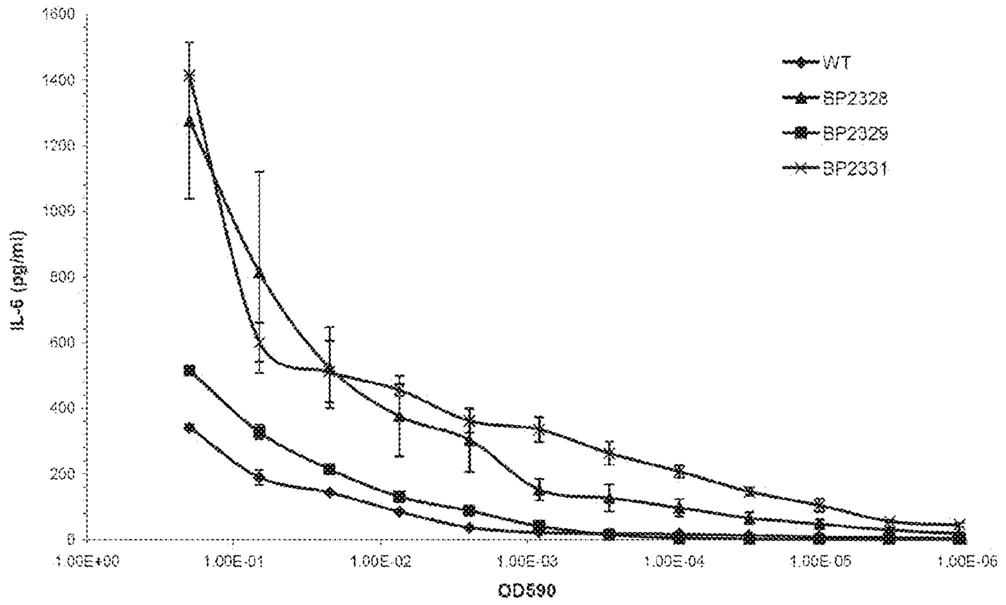

To assess the consequences of the LPS mutations on the endotoxic activity of LPS, the potency of the purified LPS to stimulate the human macrophage cell line MM6 for IL-6 production was tested. As compared with wild-type LPS, purified LPS from the BP2331-mutant strain had a strongly increased potency to stimulate the macrophages (FIG. 6A). In contrast, LPS from the BP2329-mutant strain had a reduced potency to stimulate IL-6 production, whereas LPS from the BP2328 mutant was similarly active as wild-type LPS (FIG. 6A). Only at the two highest LPS concentrations tested, the latter LPS was more active than wild-type LPS was. Consistent with the data obtained with purified LPS, whole-cell suspensions of the BP2331 mutant showed, as compared to wild-type cells, a clearly increased potency to stimulate the macrophages (FIG. 6B). However, also the BP2328-mutant cells showed this effect (FIG. 6B), while BP2329-mutant cells had similar activity as the wild-type cells in spite of their less active purified LPS (FIG. 6A).

Discussion

The goal of the present study was to identify new LPS glycosyltransferases in the *B. pertussis* genome. By using sequences of known LPS glycosyltransferases as leads, we were able to identify a four-gene operon. In a previous study, in which the genome sequence of the poultry pathogen *Bordetella avium* was compared to the genome sequences of other Bordetellae, an gene cluster homologous to the one here identified was described as being involved in LPS biosynthesis (Sebaihia et al., 2006). However, no functional studies were reported which could confirm this assignment.

To study the role of this operon in *B. pertussis* LPS biosynthesis, we inactivated the putative glycosyltransferase genes by allelic exchange and compared the LPS profiles of the wild-type and mutant strains using Tricine-SDS-PAGE and ESI-MS. Unexpectedly, we found that the wild-type strain not only contained full-length *B. pertussis* LPS, but also harboured a full-length species substituted with an extra hexosamine moiety, which, as we showed, was directly attached to lipid A. Substitution of *B. pertussis* lipid A with hexosamine has previously not been observed and therefore represents a novel modification of *B. pertussis* lipid A.

Figure 7:
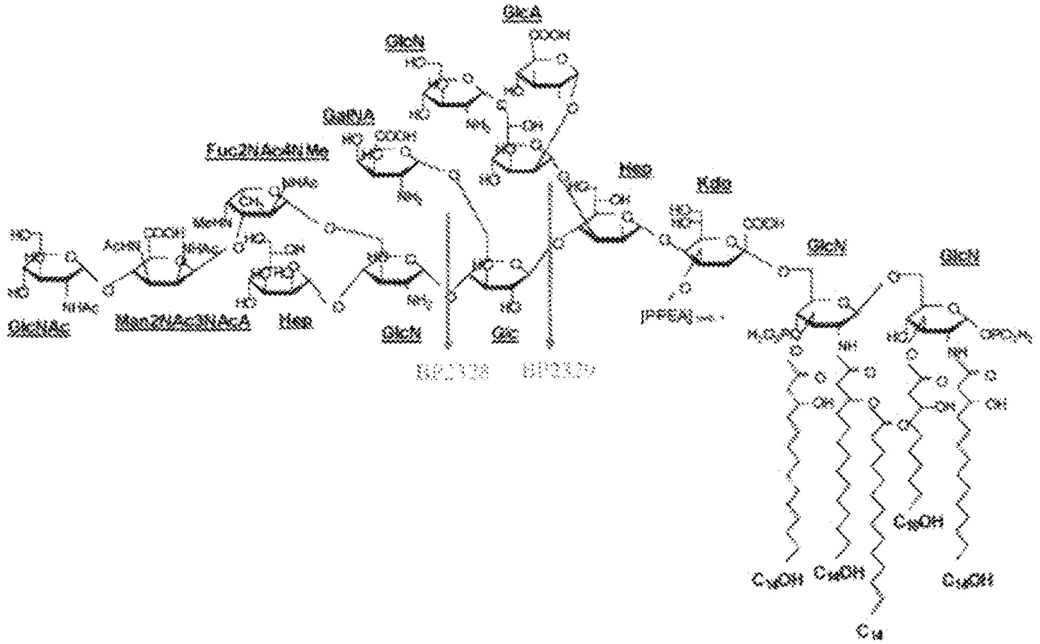
FIG. 7. Structure of *B. pertussis* LPS. Proposed truncated core OS structures of the BP2328- and BP2329-mutant strains are indicated by red arrows. Adapted from Caroff et al. (2000).

The proposed truncated oligosaccharide structures for the BP2328- and BP2329-mutant strains are summarised in FIG. 7. The most complete core OS structure in the BP2328 mutant strain consisted of GalNA•Glc•$GlcN_2$•GlcA•$Hep_2$• P•Kdo•lipid A-OH•HexN, indicating that the BP2328 mutant strain lacks the terminal trisaccharide, a heptose residue, and one of the GlcN residues. This composition suggests that the BP2328-encoded protein functions as a GlcN (1-4) to Glc transferase (FIG. 7). Analysis of the BP2329-mutant LPS showed that this LPS was further truncated and that its most complete structure consisted of GlcN•GlcA•$Hep_2$•P•Kdo•lipid A-OH•HexN. Since this structure misses the Glc to which the second GlcN of the core OS should be connected, the remaining GlcN residue present must be attached to the second heptose. Therefore, this composition suggests that the BP2329-encoded protein functions as a glucosyltransferase that attaches Glc to the first heptose subunit (FIG. 7). This would agree with the high homology of this gene product with glucose (β1-4) heptose transferases, such as rfaK and lgtF/icsB, which were used to identify the gene in the first place. The most complicated phenotype was observed in the case of the BP2331 mutant. Although the protein shows high sequence similarity to various LPS glycosyltransferases, full-length *B. pertussis* LPS was still present in the mutant strain. This observation suggests either that the BP2331 gene does not encode an active LPS glycosyltransferase or that the encoded enzyme shows redundancy. Consistent with this last option, we have identified a gene, i.e., BP3671 with GenBank Accession Number CAE43928, in the genome of *B. pertussis* which encodes for a protein that shows 69% identity to the BP2331-encoded protein. Albeit the LPS profiles of the wild-type and BP2331-mutant strain were more or less comparable, one striking observation was that the mutant LPS was more heterogenic. Although the exact reason for this phenomenon remains to be elucidated, one possible explanation could be that the BP2331 mutant somehow displays an increased non-stoichiometrical substitution of its LPS, possibly with hexosamine. Modification of lipid A with amino sugars has been described in various bacteria, e.g., substitution with 4-aminoarabinose in *E. coli* and *Salmonella* (Trent et al., 2001b), and with galactosamine in *Francisella tularensis* (Phillips et al., 2004). The aminoarabinose pathway has been studied in detail in *E. coli* and has been shown to involve the assembly of the sugar moiety on a separate undecaprenyl phosphate carrier prior to its transfer to lipid A (Trent et al., 2001a). Since it is conceivable that insertion of the kanamycin-resistance cassette in BP2331 has increased the expression of the downstream BP2330 gene, one could speculate that an increased BP2330 expression may have led to an increased hexosamine modification of lipid A, and, consequently, an increased LPS heterogeneity in the BP2331-mutant cells. Supporting this interpretation is the increased level of hexosamine modification in the BP2331 mutant, see Table 3.

After having addressed the structure of the LPS, purified LPS and whole bacterial cells were tested for their ability to induce maturation of DCs and to stimulate the production of pro-inflammatory cytokines by human macrophages. The results showed that, as compared to the wild-type strain, the BP2331-mutant strain displayed an increased capacity to induce DC maturation and pro-inflammatory cytokine production. Similar outcomes were obtained with purified LPS. In contrast, whole bacterial cells and purified LPS from the BP2328- and BP2329-mutant strains displayed a similar and decreased capacity to maturate DCs and stimulate macrophages, respectively. These results show that alterations in LPS core OS-composition differentially affect the biological properties of *B. pertussis* LPS. From the perspective of vaccine development, this is an interesting finding, since this may allow for the development of strains that more efficiently prime immune responses. Furthermore, mutants that display an increased LPS heterogeneity, such as the BP2331-mutant strain, may elicit a larger variety of anti-LPS antibodies, which, on itself, may positively influence vaccine efficacy. The good correlation found between the level of DC and macrophage activation on the one hand, and the degree of hexosamine modification of lipid A on the other (see Table 3), strongly suggests that the increased modification in the BP2331 mutant is crucial in this regard.

TABLE 1

Bacterial strains and plasmids

| Strain or plasmid | Genotype or description | Source or reference |
|---|---|---|
| Strains | | |
| *B. pertussis* | | |
| B213 | Streptomycin resistant derivative of *B. pertussis* strain Tohama | Kasuga et al., 1953 |
| B213 ΔBP2328 | BP2328 mutant of strain B213, $Str^R$, $Km^R$ | This study |
| B213 ΔBP2329 | BP2329 mutant of strain B213, $Str^R$, $Km^R$ | This study |
| B213 ΔBP2331 | BP2331 mutant of strain B213, $Str^R$, $Km^R$ | This study |
| *E. coli* | | |
| TOP10F' | F'{$lacI^q$ Tn10 ($Tet^R$)} mcrA Δ(mrr-hsdRMS-mcrBC) Φ80lacZΔM15 ΔlacX74 deoR recA1 araD139 Δ (ara-leu)7697 galU galK rpsL endA1 nupG | Invitrogen |
| DH5α | F Δ(lacZYA-algF)U169 thi-1 hsdR17 gyrA96 recA1 endA1 supE44 relA1 phoA Φ80 dlacZΔM15 | Hanahan, 1983 |
| SM10(λpir) | thi thr leu fhyA lacY supE recA::RP4-2-Tc::Mu λ pir R6K $Km^R$ | N.V.I.[a] |
| Plasmids | | |
| pGEM-T Easy | *E. coli* cloning vector $Amp^R$ | Promega |
| pUC4K | *E. coli* vector harbouring kanamycin-resistance cassette, $Amp^R$ $Km^R$ | Vieira and Messing, 1982 |
| pSS1129 | Allelic exchange vector, bla gen rpsL oriVColE1 oriT λ cos | Stibitz, 1994 |
| pGEM-$BP2328_{up}$ | pGEM-T Easy derivative harbouring BP2328 upstream sequence | This study |
| pGEM-$BP2328_{down}$ | pGEM-T Easy derivative harbouring BP2328 downstream sequence | This study |
| pGEM-$BP2329_{up}$ | pGEM-T Easy derivative harbouring BP2329 upstream sequence | This study |
| pGEM-$BP2329_{down}$ | pGEM-T Easy derivative harbouring BP2329 downstream sequence | This study |
| pGEM-BP2331 | pGEM-T Easy derivative harbouring BP2331 sequence | This study |
| pSS1129-$BP2328_{KO}$ | pSS1129 derivative harbouring BP2328 knock out construct, $Km^R$ | This study |
| pSS1129-$BP2329_{KO}$ | pSS1129 derivative harbouring BP2329 knock out construct, $Km^R$ | This study |
| pSS1129-$BP2331_{KO)}$ | pSS1129 derivative harbouring BP2331 knock out construct, $Km^R$ | This study |

[a]Netherlands Vaccine Institute, Bilthoven, The Netherlands

TABLE 2

| Primers | | |
|---|---|---|
| Name | Sequence (5'-3')[a] | |
| BP2328_FW$_{up}$ | TTCCGCACTTACTGGCTGAG | SEQ ID NO: 5 |
| BP2328_FW$_{down}$ | GGATCCTCGCGGTACGACAGCACAT | SEQ ID NO: 6 |
| BP2328_REV$_{up}$ | GGATCCTGTTGCGCGAGATGCTGGAG | SEQ ID NO: 7 |
| BP2328_REV$_{down}$ | CCTCATCGCCAAGGTCAATC | SEQ ID NO: 8 |
| BP2329_FW$_{up}$ | TCACCTTCGACGACGGATAC | SEQ ID NO: 9 |
| BP2329_FW$_{down}$ | GGATCCGTGCGCATCTACCTGATCC | SEQ ID NO: 10 |
| BP2329_REV$_{up}$ | GGATCCGAATCGACCACGATGAAC | SEQ ID NO: 11 |
| BP2329_REV$_{down}$ | GATCCAGCTTGGCCTGGTTG | SEQ ID NO: 12 |
| BP2331_FW | GTGACGTGGTGGTACATCAG | SEQ ID NO: 13 |
| BP2331_REV | TGGTCTACCGCAGGAACAAT | SEQ ID NO: 14 |

[a]BamHI restriction sites are underlined

TABLE 3

Negative ion ESI-MS data and proposed compositions for O-deacylated LPS of wild-type *B. pertussis* and *B. pertussis* mutant strains BP2331, BP2328, and BP239. Average mass units were used for calcuation of molecular mass values based on proposed compositions as follows: glucose (Glc), 162.14; heptose (Hep), 192.17; 2-keto-3-deoxyoctulosonic acid (Kdo), 220.18; phosphate (P), 79.98; glucosamine (GlcN), 161.17; hexosamine (HexN), 161.17; glucuronic acid (GlcA), 176.13; N-acetyl-glucosamine (GlcNAc), 203.19; 2-acetamido-4-N-methyl-2,4-dideoxy-fucose (Fuc2NAc4NMe), 200.12; 2,3-acetamido-2,3-dideoxy-mannuronicacid (Man2NAc3NAcA), 258.09; galactosaminuronic acid (GalNA), 175.13 and lipid A-OH, 953.02. Table does not include sodium and potassium adducts and singly-charged lipid A-OH ions (m/z 952 ($[M-H]^-$)).

| | Observed ions [m/z] | | | Molecular mass [Da] | | Relative abundance | |
|---|---|---|---|---|---|---|---|
| Sample | $[M-4H]^{4-}$ | $[M-3H]^{3-}$ | $[M-2H]^{2-}$ | Observed | Calculated | [%] | Proposed composition |
| WT | | | 987.1 | 1976.2 | 1975.8 | 16.6 | Glc•GlcA•Hep$_2$•P•Kdo•lipid A-OH |
| | | 770.1 | 1155.0 | 2312.7 | 2312.1 | 12.8 | GalNA•Glc•GlcN•GlcA•Hep$_2$•P•Kdo•lipid A-OH |
| | | 888.3 | | 2667.9 | 2665.4 | 4.9 | GalNA•Glc•GlcN$_2$•GlcA•Hep$_3$•P•Kdo•lipid A-OH |
| | 811.1 | 1081.7 | | 3248.3 | 3246.9 | 11.8 | GlcNAc•Man2NAc3NAcA•Fuc2NAc4NMe•GalNA•Glc•GlcN$_2$•GlcA•Hep$_3$•Kdo•lipid A-OH |
| | 831.4 | 1108.5 | | 3329.0 | 3326.8 | 27.4 | GlcNAc•Man2NAc3NAcA•Fuc2NAc4NMe•GalNA•Glc•GlcN$_2$•GlcA•Hep$_3$•P•Kdo•lipid A-OH |
| | | | | | | 9.8 | GlcNAc•Man2NAc3NAcA•Fuc2NAc4NMe•GalNA•Glc•GlcN•GlcA•Hep$_3$•P•Kdo•lipid A-OH•HexN |
| | | 1162.1 | | 3489.3 | 3488.0 | 16.7 | GlcNAc•Man2NAc3NAcA•Fuc2NAc4NMe•GalNA•Glc•GlcN$_2$•GlcA•Hep$_3$•P•Kdo•lipid A-OH•HexN |
| BP2328 | | 743.6 | 1115.2 | 2233.1 | 2232.1 | 13.8 | GalNA•Glc•GlcN•GlcA•Hep$_2$•Kdo•lipid A-OH |
| | | 770.0 | 1155.1 | 2312.6 | 2312.1 | 46.5 | GalNA•Glc•GlcN•GlcA•Hep$_2$•P•Kdo•lipid A-OH |
| | | | | | | 15.3 | GalNA•Glc•GlcA•Hep$_2$•P•Kdo•lipid A-OH•HexN |
| | | 823.7 | 1235.7 | 2473.8 | 2473.3 | 12.1 | GalNA•Glc•GlcN•GlcA•Hep$_2$•P•Kdo•lipid A-OH•HexN |
| | | | 1034.6 | 2071.2 | 2070.8 | 6.7 | GalNA•Glc•GlcA•Hep$_2$•Kdo•lipid A-OH |
| | | | 1074.6 | 2151.2 | 2150.8 | 5.6 | GalNA•Glc•GlcA•Hep$_2$•P•Kdo•lipid A-OH |

TABLE 3-continued

Negative ion ESI-MS data and proposed compositions for O-deacylated LPS of wild-type *B. pertussis* and *B. pertussis* mutant strains BP2331, BP2328, and BP239. Average mass units were used for calcuation of molecular mass values based on proposed compositions as follows: glucose (Glc), 162.14; heptose (Hep), 192.17; 2-keto-3-deoxyoctulosonic acid (Kdo), 220.18; phosphate (P), 79.98; glucosamine (GlcN), 161.17; hexosamine (HexN), 161.17; glucuronic acid (GlcA), 176.13; N-acetyl-glucosamine (GlcNAc), 203.19; 2-acetamido-4-N-methyl-2,4-dideoxy-fucose (Fuc2NAc4NMe), 200.12; 2,3-acetamido-2,3-dideoxy-mannuronicacid (Man2NAc3NAcA), 258.09; galactosaminuronic acid (GalNA), 175.13 and lipid A-OH, 953.02. Table does not include sodium and potassium adducts and singly-charged lipid A-OH ions (m/z 952 ($[M - H]^-$)).

| | Observed ions [m/z] | | | Molecular mass [Da] | | Relative abundance | |
|---|---|---|---|---|---|---|---|
| Sample | $[M - 4H]^{4-}$ | $[M - 3H]^{3-}$ | $[M - 2H]^{2-}$ | Observed | Calculated | [%] | Proposed composition |
| BP2329 | | | 866.0 | 1734.0 | 1733.7 | 8.6 | GlcA•$Hep_2$•Kdo•lipid A-OH |
| | | 603.9 | 906.0 | 1814.4 | 1813.6 | 36.8 | GlcA•$Hep_2$•P•Kdo•lipid A-OH |
| | | 657.6 | 986.6 | 1975.5 | 1974.8 | 28.8 | GlcN•GlcA•$Hep_2$•P•Kdo•lipid A-OH |
| | | | | | | 8.4 | GlcA•$Hep_2$•P•Kdo•lipid A-OH•HexN |
| | | | 1067.1 | 2136.2 | 2136.0 | 6.6 | GlcN•GlcA•$Hep_2$•P•Kdo•lipid A-OH•HexN |
| BP2331 | | 684.9 | 1027.5 | 2057.4 | 2057.0 | 16.3 | Glc•GlcN•GlcA•$Hep_2$•Kdo•lipid A-OH |
| | | | | | | 4.3 | Glc•GlcA•$Hep_2$•Kdo•lipid A-OH•HexN |
| | | 711.5 | 1067.4 | 2137.2 | 2137.0 | 6.4 | Glc•GlcN•GlcA•$Hep_2$•P•Kdo•lipid A-OH |
| | | | | | | 6.1 | Glc•GlcA•$Hep_2$•P•Kdo•lipid A-OH•HexN |
| | | 738.5 | | 2218.5 | 2218.2 | 3.7 | Glc•GlcN•GlcA•$Hep_2$•Kdo•lipid A-OH•HexN |
| | | 765.2 | 1148.0 | 2298.3 | 2298.1 | 6.3 | Glc•GlcN•GlcA•$Hep_2$•P•Kdo•lipid A-OH•HexN |
| | | | 1291.6 | 2585.2 | 2585.5 | 4.1 | GalNA•Glc•$GlcN_2$•GlcA•$Hep_3$•Kdo•lipid A-OH |
| | | | | | | 4.9 | GalNA•Glc•GlcN•GlcA•$Hep_3$•Kdo•lipid A-OH•HexN |
| | | 887.8 | 1332.0 | 2666.2 | 2665.4 | 5.6 | GalNA•Glc•$GlcN_2$•GlcA•$Hep_3$•P•Kdo•lipid A-OH |
| | | | | | | 4.2 | GalNA•Glc•GlcN•GlcA•$Hep_3$•P•Kdo•lipid A-OH•HexN |
| | 810.9 | 1081.7 | | 3247.9 | 3246.9 | 9.8 | GlcNAc•Man2NAc3NAcA•Fuc2NAc4NMe•GalNA•Glc•$GlcN_2$•GlcA•$Hep_3$•Kdo•lipid A-OH |
| | 831.1 | 1108.3 | | 3328.2 | 3326.8 | 11.7 | GlcNAc•Man2NAc3NAcA•Fuc2NAc4NMe•GalNA•Glc•$GlcN_2$•GlcA•$Hep_3$•P•Kdo•lipid A-OH |
| | | | | | | 7.3 | GlcNAc•Man2NAc3NAcA•Fuc2NAc4NMe•GalNA•Glc•GlcN•GlcA•$Hep_3$•P•Kdo•lipid A-OH•HexN |
| | 871.2 | 1162.0 | | 3488.9 | 3488.0 | 9.3 | GlcNAc•Man2NAc3NAcA•Fuc2NAc4NMe•GalNA•Glc•$GlcN_2$•GlcA•$Hep_3$•P•Kdo•lipid A-OH•HexN |

References

Alexeyev, M. F., Shokolenko, I. N., and Croughan, T. P. (1995) Improved antibiotic-resistance gene cassettes and omega elements for *Escherichia coli* vector construction and in vitro deletion/insertion mutagenesis. *Gene* 160: 63-67.

Allen, A. G., Isobe, T., and Maskell, D. J. (1998a) Identification and cloning of waaF (rfaF) from *Bordetella pertussis* and use to generate mutants of *Bordetella* spp. with deep rough lipopolysaccharide. *J. Bacteriol.* 180: 35-40.

Allen, A. G., Thomas, R. M., Cadisch, J. T., and Maskell, D. J. (1998b) Molecular and functional analysis of the lipopolysaccharide biosynthesis locus wlb from *Bordetella pertussis, Bordetella parapertussis* and *Bordetella bronchiseptica*. *Mol. Microbiol.* 29: 27-38.

Allen, A., and Maskell, D. (1996) The identification, cloning and mutagenesis of a genetic locus required for lipopolysaccharide biosynthesis in *Bordetella pertussis*. *Mol. Microbiol.* 19: 37-52.

Caroff, M., Brisson, J., Martin, A., and Karibian, D. (2000) Structure of the *Bordetella pertussis* 1414 endotoxin. *FEBS Lett.* 477: 8-14.

Clementz, T., and Raetz, C. R. H. (1991) A gene coding for 3-deoxy-D-manno-octulosonic-acid transferase in *Escherichia coli*. Identification, mapping, cloning, and sequencing. *J. Biol. Chem.* 266: 9687-9696.

Di Fabio, J. L., Caroff, M., Karibian, D., Richards, J. C., and Perry, M. B. (1992) Characterisation of the common antigenic lipopolysaccharide O-chains produced by *Bordetella bronchiseptica* and *Bordetella parapertussis*. *FEMS Microbiol. Lett.* 76: 275-281.

Geurtsen, J., Steeghs, L., Hamstra, H-J., ten Hove, J., de Haan, A., Kuipers, B., Tommassen, J., and van der Ley, P. (2006) Expression of the lipopolysaccharide-modifying enzymes PagP and PagL modulates the endotoxic activity of *Bordetella pertussis*. *Infect. Immun.* 74: 5574-5585.

Hanahan, D. (1983) Studies on transformation of *Escherichia coli* with plasmids. *J. Mol. Biol.* 166: 557-580.

Hoist, O. (2000) Deacylation of lipopolysaccharides and isolation of oligosaccharides phosphates. in *Methods in Molecular Biology, Bacterial Toxins: Methods and Protocols* (Holst, O., Ed.) pp 345-353, Humana Press, Totowa, N.J.

Heinrichs, D. E., Yethon, J. A., and Whitfield, C. (1998) Molecular basis for structural diversity in the core regions of the lipopolysaccharides of *Escherichia coli* and *Salmonella enterica. Mol. Microbiol.* 30: 221-232.

Isobe, T., White, K. A., Allen, A. G., Peacock, M., Raetz, C. R. H., and Maskell, D. J. (1999) *Bordetella pertussis* waaA encodes a monofunctional 2-keto-3-deoxy-D-manno-octulosonic acid transferase that can complement an *Escherichia coli* waaA mutation. *J. Bacteriol.* 181: 2648-2651.

Kasuga, B., Nakase, Y., Ukishima, K., and Takatsu, K. (1953) Studies on *Haemophilus pertussis. Kitasato Arch. Exp. Med.* 27: 21-28.

Kurzai, O., Schmitt, C., Claus, H., Vogel, U, Frosch, M, and Kolb-Maurer, A. (2005) Carbohydrate composition of meningococcal lipopolysaccharide modulates the interaction of *Neisseria meningitidis* with human dendritic cells. *Cell. Microbiol.* 7: 1319-1334.

Laemmli, U. K. (1970) Cleavage of structural proteins during the assembly of the head of bacteriophage T4. *Nature* 227: 680-685.

Lesse, A. J., Campagnari, A. A., Bittner, W. E., and Apicella, M. A. (1990) Increased resolution of lipopolysaccharides and lipooligosaccharides utilizing tricine-sodium dodecyl sulfate-polyacrylamide gel electrophoresis. *J. Immunol. Methods* 126: 109-117.

MacLachlan, P. R., Kadam, S. K., and Sanderson, K. E. (1991) Cloning, characterization, and DNA sequence of the rfaLK region for lipopolysaccharide synthesis in *Salmonella typhimurium* LT2. *J. Bacteriol.* 173: 7151-7163.

O'Neill, L. A. J. (2006) How Toll-like receptors signal: what we know and what we don't know. *Curr. Opin. Immunol.* 18: 3-9.

Pålsson-McDermott, E. M., and O'Neill, L. A. J. (2004) Signal transduction by the lipopolysaccharide receptor, Toll-like receptor-4. *Immunology* 113: 153-162.

Peppler, M. S. (1984) Two physically and serologically distinct lipopolysaccharide profiles in strains of *Bordetella pertussis* and their phenotype variants. *Infect. Immun.* 43: 224-232.

Phillips, N. J., Schilling, B., McLendon, M. K., Apicella, M. A., and Gibson, B. W. (2004) Novel modification of lipid A of *Francisella tularensis. Infect. Immun.* 72: 5340-5348.

Plüiddeman, A., Mukhopadhyay, S., and Gordon, S. (2006) The interaction of macrophage receptors with bacterial ligands. *Exp. Rev. Mol. Med.* 8: 1-25.

Raetz, C. R. H., and Whitfield, C. (2002) Lipopolysaccharide endotoxins. *Annu. Rev. Biochem.* 71: 635-700.

Sallusto, F., and Lanzavecchia, A. (1994) Efficient presentation of soluble antigen by cultured human dendritic cells is maintained by granulocyte/macrophage colony-stimulating factor plus interleukin 4 and downregulated by tumor necrosis factor α. *J. Exp. Med.* 179: 1109-1118.

Schnaitman, C. A., and Klena, J. D. (1993) Genetics of lipopolysaccharide biosynthesis in enteric bacteria. *Microbiol. Rev.* 57: 655-682.

Sisti, F., Fernandez, J., Rodriguez, M. E., Lagares, A., Guiso, N., and Hozbor, D. F. (2002) In vitro and in vivo characterization of a *Bordetella bronchiseptica* mutant strain with a deep rough lipopolysaccharide structure. *Infect. Immun.* 70: 1791-1798.

Steeghs, L., van Vliet, S. J., Uronen-Hansson, H., van Mourik, A., Engering, A., Sanchez-Hernandez, M., Klein, N., Callard, R., van Putten, J. P. M., van der Ley, P., van Kooyk, Y., and van de Winkel, J. G. J. (2006) *Neisseria meningitidis* expressing lgtB lipopolysaccharide targets DC-SIGN and modulates dendritic cell function. *Cell. Microbiol.* 8: 316-325.

Stibitz, S. (1994) Use of conditionally counterselectable suicide vectors for allelic exchange.

*Methods Enzymol.* 235: 458-465.

Takada H, and Kotani S. (1989) Structural requirements of lipid A for endotoxicity and other biological activities. *Crit. Rev. Microbiol.* 16: 477-523.

Trent, M. S., Ribeiro, A. A., Doerrler, W. T., Lin, S., Cotter, R. J., and Raetz, C. R. H. (2001a) Accumulation of a polyisoprene-linked amino sugar in polymyxin-resistant *Salmonella typhimurium* and *Escherichia coli*: structural characterization and transfer to lipid A in the periplasm. *J. Biol. Chem.* 276: 43132-43144.

Trent, M. S., Ribeiro, A. A., Lin, S., Cotter, R. J., and Raetz, C. R. H. (2001b) An inner membrane enzyme in *Salmonella* and *Escherichia coli* that transfers 4-amino-4-deoxy-L-arabinose to lipid A: induction on polymyxin-resistant mutants and role of a novel lipid-linked donor. *J. Biol. Chem.* 276: 43122-43131.

Tsai, C. M., and Frasch, C. E. (1982) A sensitive silver stain for detecting lipopolysaccharides in polyacrylamide gels. *Anal. Biochem.* 119: 115-119.

Uronen-Hansson, H., Steeghs, L., Allen, J., Dixon, G. L. J., Osman, M., van der Ley, P., Wong, S. Y. C., Callard, R., and Klein, N. (2004) Human dendritic cell activation by *Neisseria meningitidis*: phagocytosis depends on expression of lipooligosaccharide (LOS) by the bacteria and is required for optimal cytokine production. *Cell. Microbiol.* 6: 625-637.

van Amersfoort, E. S., Van Berkel, T. J., and Kuiper, J. (2003) Receptors, mediators, and mechanisms involved in bacterial sepsis and septic shock. *Clin. Microbiol. Rev.* 16: 379-414.

Westphal, O., and Jann, J. K. (1965) Bacterial lipopolysaccharides, extraction with phenol-water and further applications of the procedure. *Methods Carbohydr. Chem.* 5: 83-91.

Ziegler-Heitbrock, H. W. L., Thiel, E., Futterer, A., Herzog, V., Wirtz, A., and Riethmüller, G. (1988) Establishment of a human cell line (Mono Mac 6) with characteristics of mature monocytes. *Int. J. Cancer* 41: 456-461.

The invention claimed is:

1. A mutant cell of a wild-type parental *Bordetella pertussis* cell, of a wild-type parental *Bordetella bronchiseptica* cell, or of a wild-type parental *Bordetella parapertussis* cell comprising a mutated nucleic acid sequence, wherein:

(a) the wild-type *Bordetella pertussis* cell, the wild-type *Bordetella bronchiseptica* cell, or the wild-type *Bordetella parapertussis* cell comprises an endogenous nucleic acid sequence encoding an endogenous lipopolysaccharide (LPS) glycosyltransferase polypeptide, wherein the polypeptide has at least 99% sequence identity with SEQ ID NO: 2 and (b) the mutated nucleic acid sequence (i) encodes a mutant LPS glycosyltransferase polypeptide having glycosyltransferase enzymatic activity that is at least 3% lower compared to the glycosyltransferase enzymatic activity of the endogenous LPS glycosyltransferase polypeptide of (a), or (ii) results in production of at least 3% less of the endogenous LPS glycosyltransferase polypeptide of (a) by the mutant cell compared to the production of the endogenous LPS glycosyltransferase polypeptide of (a) by the wild-type *Bordetella pertussis* cell, the wild-type *Bordetella bronchiseptica* cell, or the wild-type *Bordetella parapertussis* cell when cultivated under the same culture conditions, wherein, compared to the wild-type parental cell, the mutant cell induces increased immune stimulation as determined by activation of human dendritic cells or stimulation of human macrophages.

2. The mutant cell of claim 1, wherein the endogenous nucleic acid sequence is mutated by insertional inactivation.

3. The mutant cell of claim 1, in which the mutant LPS glycosyltransferase polypeptide does not exhibit any detectable glycosyltransferase enzymatic activity.

4. The mutant cell of claim 1, wherein the amino acid sequence of said polypeptide is SEQ ID NO: 2.

5. A pharmaceutical composition comprising the mutant cell of claim 1 and a pharmaceutically acceptable carrier.

6. A pharmaceutical composition comprising the mutant cell of claim 4 and a pharmaceutically acceptable carrier.

7. The pharmaceutical composition of claim 5, further comprising an antigen.

8. The mutant cell of claim 1, wherein the LPS glycosyltransferase polypeptide of (a) produced by the mutant cell is at least 90% less compared to that produced by the wild-type *Bordetella pertussis* cell, the wild-type *Bordetella bronchiseptica* cell, or the wild-type *Bordetella parapertussis* cell.

9. The mutant cell of claim 8, wherein the amino acid sequence of said polypeptide is SEQ ID NO: 2.

10. A pharmaceutical composition comprising the mutant cell of claim 8 and a pharmaceutically acceptable carrier.

11. A pharmaceutical composition comprising the mutant cell of claim 9 and a pharmaceutically acceptable carrier.

12. The pharmaceutical composition of claim 10, further comprising an antigen.

13. A method of inducing an immune response to an antigen in a mammalian subject comprising administering to the subject the pharmaceutical composition of claim 7.

14. The pharmaceutical composition of claim 6, further comprising an antigen.

15. The pharmaceutical composition of claim 11, further comprising an antigen.

16. A method of inducing an immune response to an antigen in a mammalian subject comprising administering to the subject the pharmaceutical composition of claim 12.

17. A method of inducing an immune response to an antigen in a mammalian subject comprising administering to the subject the pharmaceutical composition of claim 14.

18. A method of inducing an immune response to an antigen in a mammalian subject comprising administering to the subject the pharmaceutical composition of claim 15.

* * * * *